United States Patent
Lebens, III

(10) Patent No.: US 10,881,414 B2
(45) Date of Patent: Jan. 5, 2021

(54) ANTI-MIGRATION SURGICAL LIGATION CLIP

(71) Applicant: Nanova Biomaterials, Inc., Columbia, MO (US)

(72) Inventor: Richard Joseph Lebens, III, Columbia, MO (US)

(73) Assignee: NANOVA BIOMATERIALS, INC., Columbia, MO (US)

( * ) Notice: Subject to any disclaimer, the term of this patent is extended or adjusted under 35 U.S.C. 154(b) by 164 days.

(21) Appl. No.: 15/736,473

(22) PCT Filed: Jun. 15, 2016

(86) PCT No.: PCT/US2016/037590
§ 371 (c)(1),
(2) Date: Dec. 14, 2017

(87) PCT Pub. No.: WO2016/205343
PCT Pub. Date: Dec. 22, 2016

(65) Prior Publication Data
US 2018/0185029 A1    Jul. 5, 2018

Related U.S. Application Data

(60) Provisional application No. 62/180,532, filed on Jun. 16, 2015.

(51) Int. Cl.
*A61B 17/08* (2006.01)
*A61B 17/122* (2006.01)
*A61B 17/00* (2006.01)

(52) U.S. Cl.
CPC .......... *A61B 17/122* (2013.01); *A61B 17/083* (2013.01); *A61B 2017/00477* (2013.01)

(58) Field of Classification Search
CPC ..... A61B 17/08; A61B 17/122; A61B 17/083; A61B 2017/00477; A61B 17/12; A61B 17/1209; A61B 17/1227
See application file for complete search history.

(56) References Cited

U.S. PATENT DOCUMENTS

| | | | |
|---|---|---|---|
| 3,363,628 A | 1/1968 | Wood | |
| 3,867,944 A | 2/1975 | Samuels | |

(Continued)

FOREIGN PATENT DOCUMENTS

| | | | |
|---|---|---|---|
| CN | 201642186 U | 11/2010 | |
| DE | 198 32 739 A1 | 2/2000 | |

(Continued)

OTHER PUBLICATIONS

Extended European Search Report dated Mar. 13, 2019, in counterpart European Application No. 16812317.2.

(Continued)

*Primary Examiner* — Vi X Nguyen
(74) *Attorney, Agent, or Firm* — Finnegan, Henderson, Farabow, Garrett, Dunner, LLP

(57) ABSTRACT

The present disclosure provides a surgical clip for ligating a blood vessel or tissue structure. The surgical clip includes a first leg member including a first inner surface and a first plurality of protrusions disposed on the first inner surfaces. The surgical clip also includes a second leg member including a second inner surface and a second plurality of protrusions disposed on the second inner surface. The surgical clip further includes a hinge member joining the first leg member and the second leg member. The at least one of the first and second plurality of protrusions includes a gable structure that extends along a longitudinal direction of the first or second inner surface. The orientation and the geometric shape of the protrusions of the surgical clip allow for increased resistance to the migration or sliding of the clip (Continued)

along a longitudinal direction of the blood vessel or tissue structure, while providing a balanced closure force. The surgical clip can prevent the longitudinal migration along the blood vessel or tissue structure.

12 Claims, 32 Drawing Sheets

(56) References Cited

U.S. PATENT DOCUMENTS

| | | |
|---|---|---|
| 3,874,042 A | 4/1975 | Eddleman et al. |
| 4,579,118 A | 4/1986 | Failla |
| 4,834,096 A | 5/1989 | Oh et al. |
| 4,976,722 A | 12/1990 | Failla |
| 5,062,846 A | 11/1991 | Oh et al. |
| 5,501,693 A | 3/1996 | Gravener |
| 5,509,920 A | 4/1996 | Phillips et al. |
| 7,326,223 B2 | 2/2008 | Wilson |
| 2008/0312670 A1* | 12/2008 | Lutze ............ A61B 17/1222 606/157 |
| 2008/0319456 A1 | 12/2008 | Hart |
| 2012/0083803 A1* | 4/2012 | Patel ............ A61B 17/122 606/142 |
| 2013/0226200 A1 | 8/2013 | Kappel et al. |

FOREIGN PATENT DOCUMENTS

| | | |
|---|---|---|
| EP | 2 392 268 A1 | 12/2011 |
| WO | WO 2014/142454 A1 | 9/2014 |

OTHER PUBLICATIONS

International Search Report and Written Opinion issued in Application No. PCT/US16/37590 dated Sep. 2, 2016.

Chinese Office Action issued by the State Intellectual Property Office (SIPO) of the People's Republic of China dated Mar. 23, 2020, in counterpart Chinese Application No. 201680036146.9.

* cited by examiner

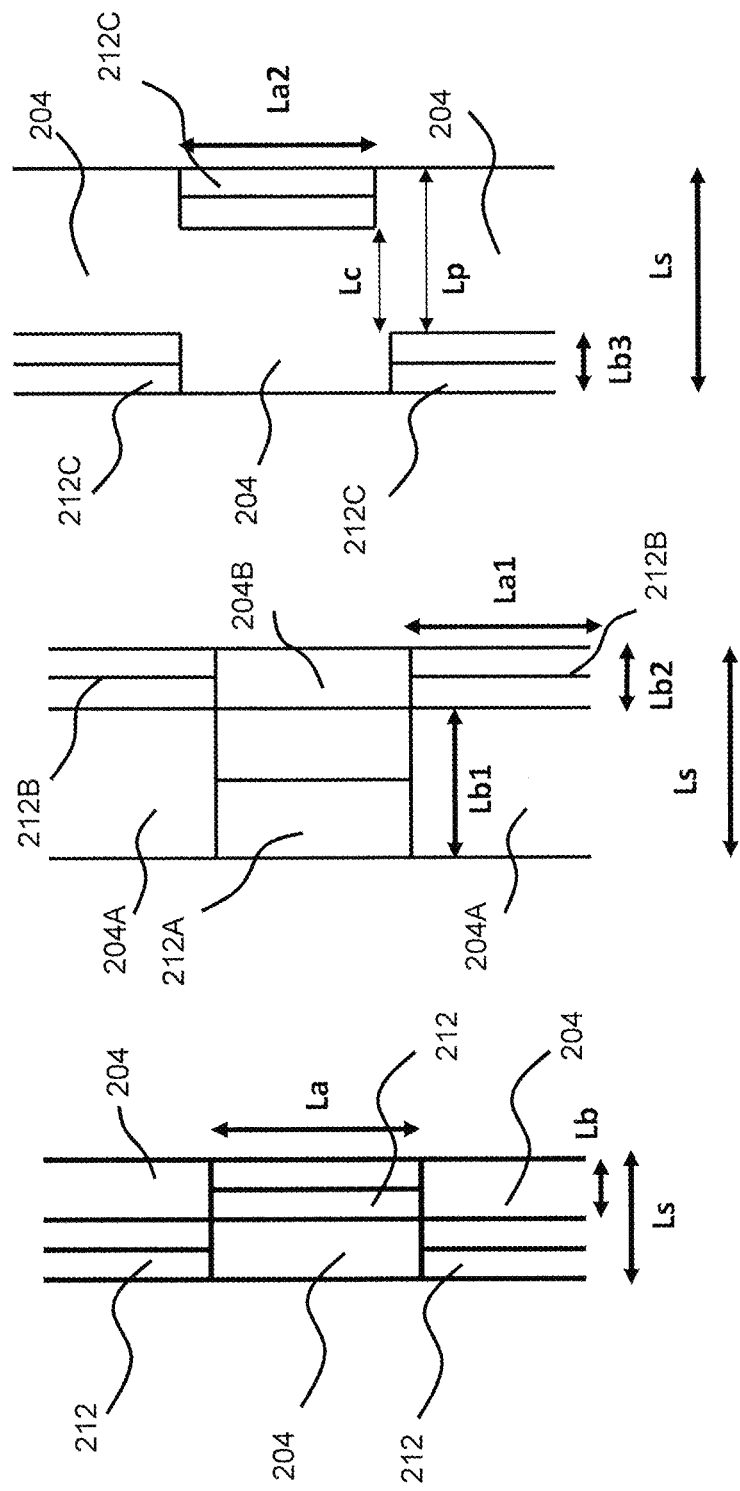

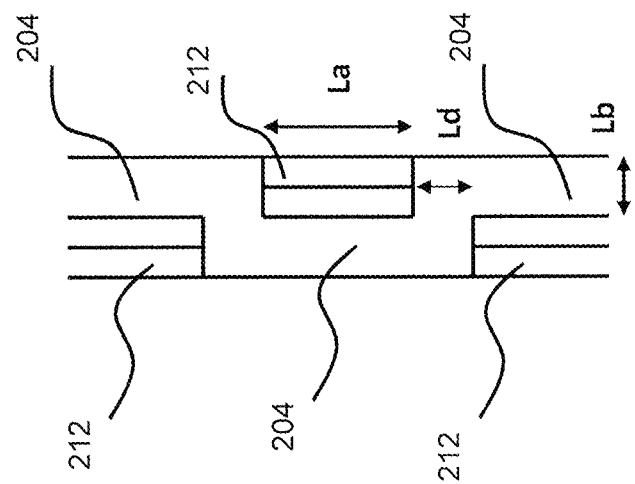
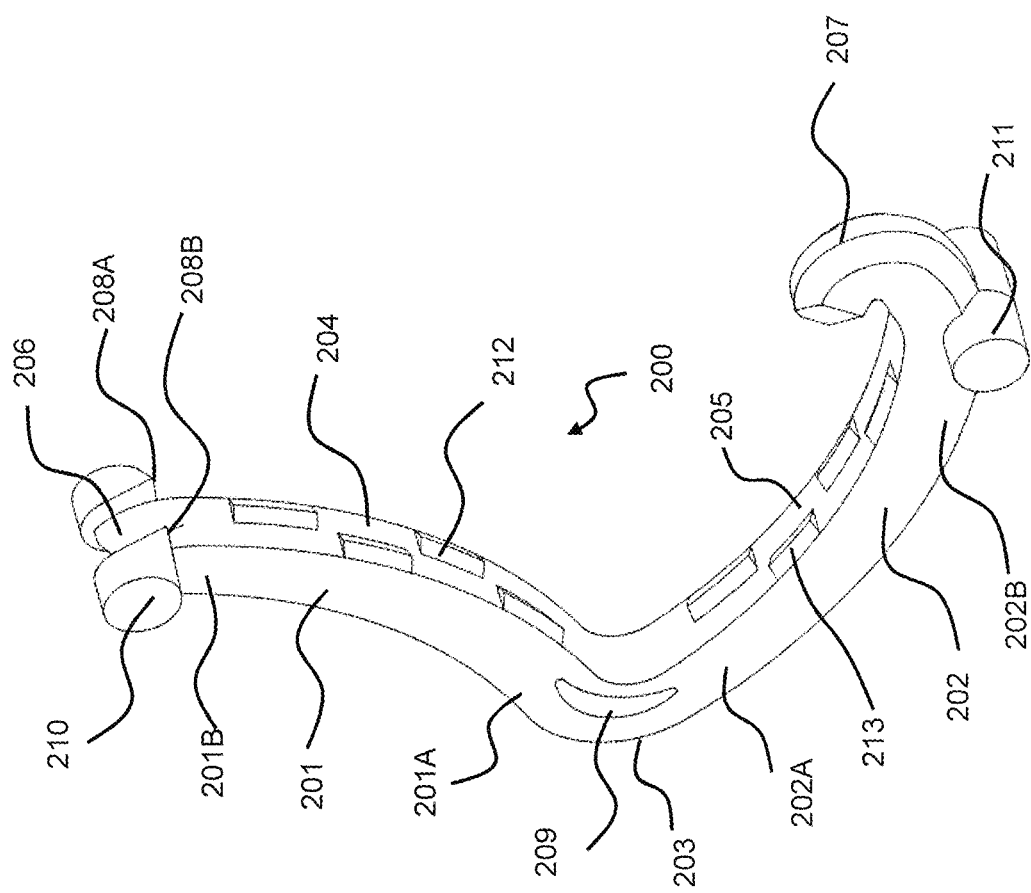

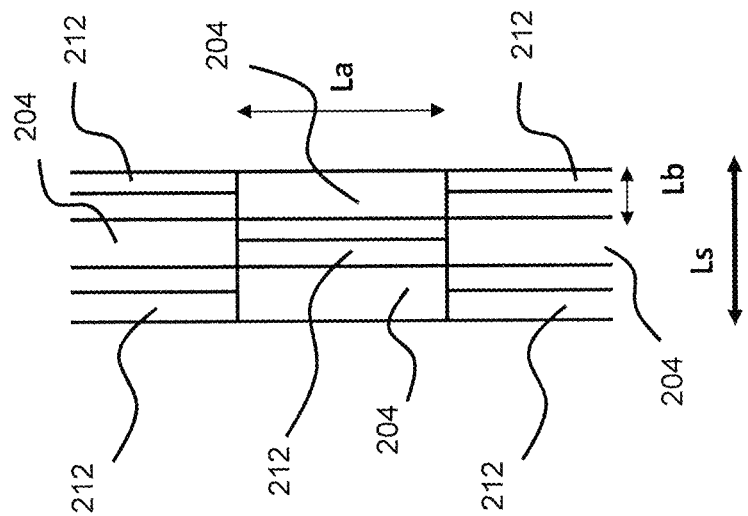
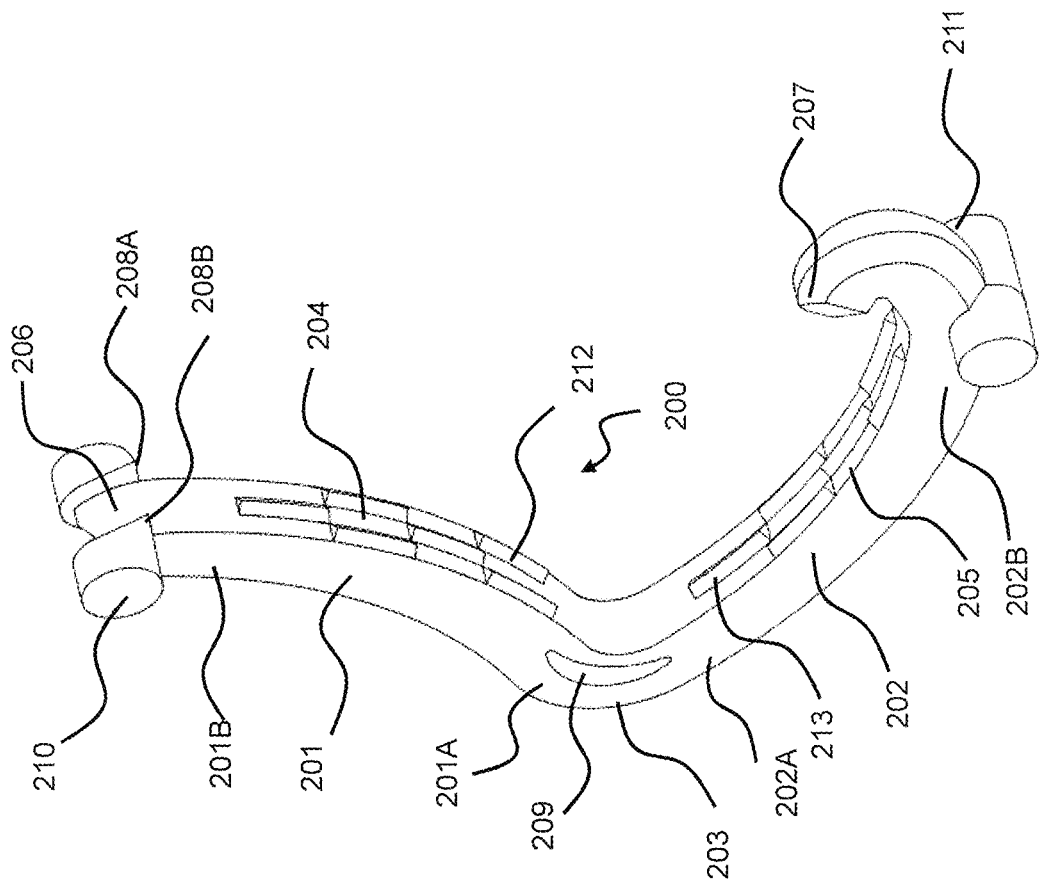
FIG. 6B
FIG. 6A

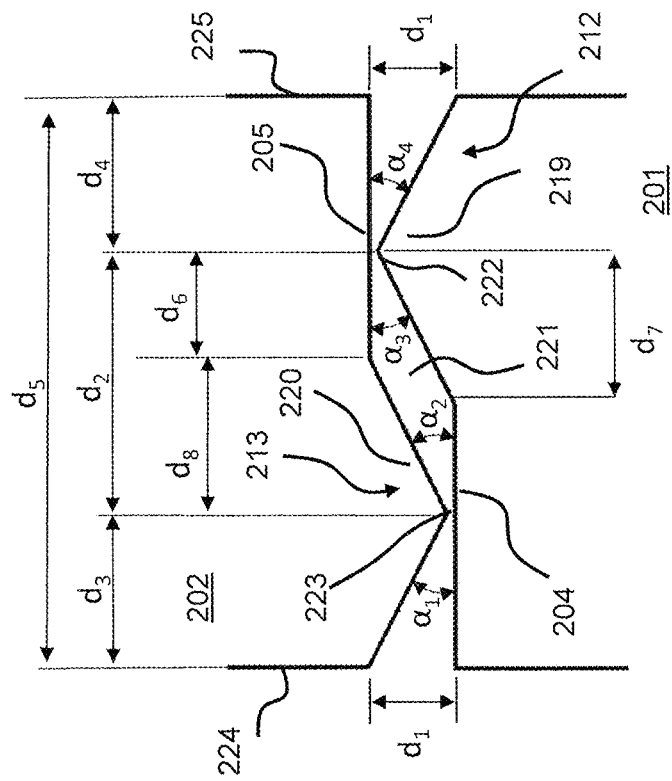
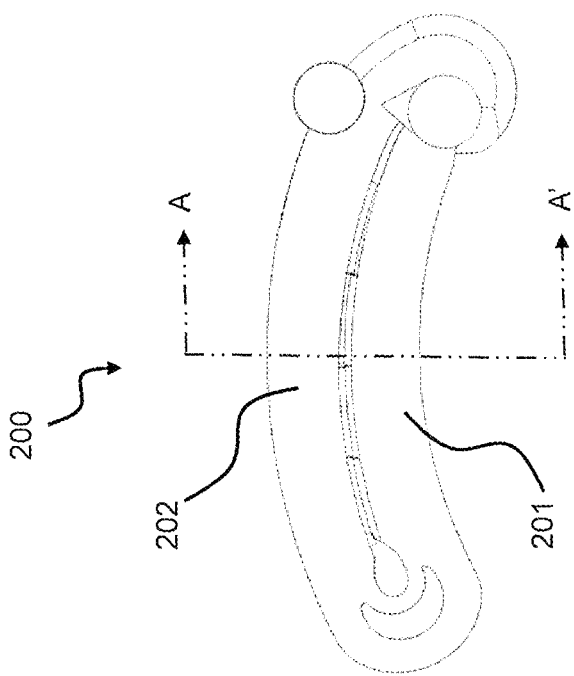
FIG. 7B
FIG. 7A

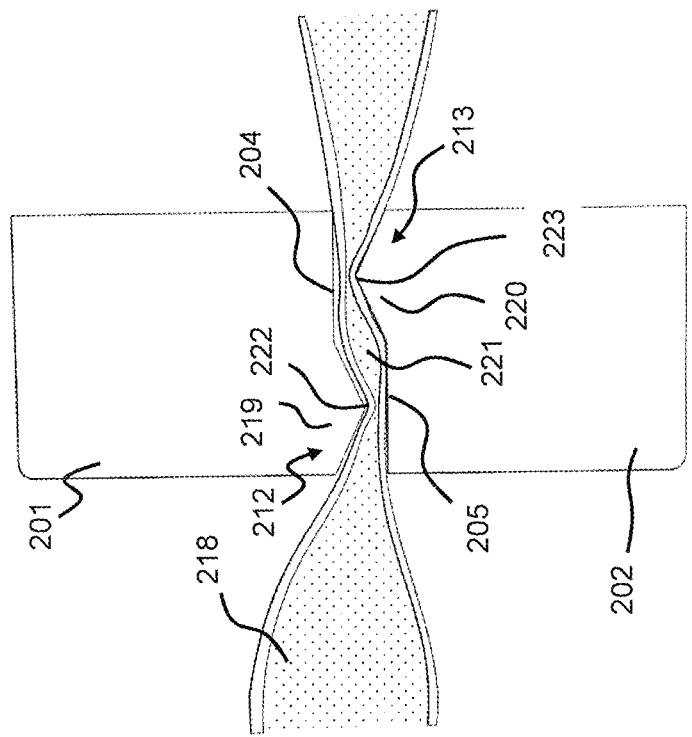
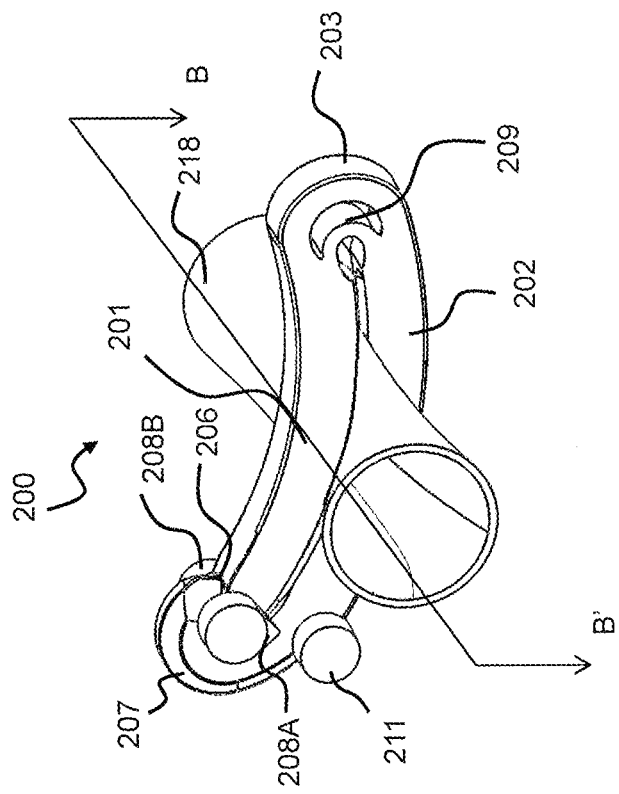
FIG. 8B
FIG. 8A

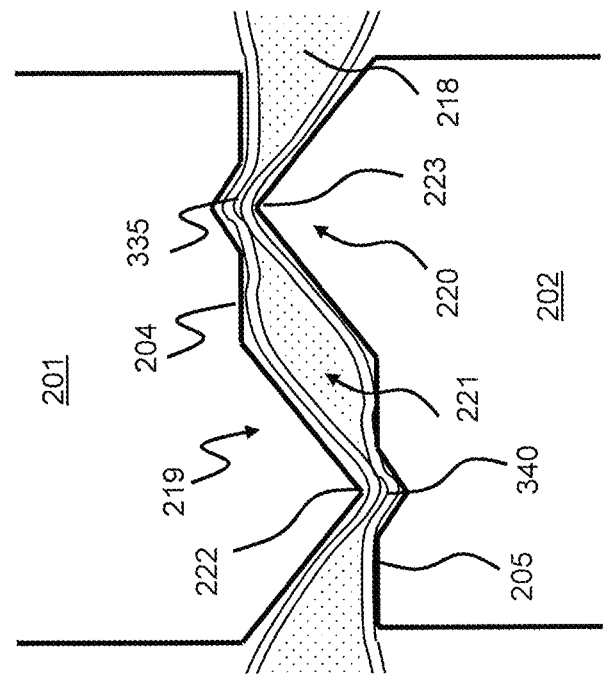
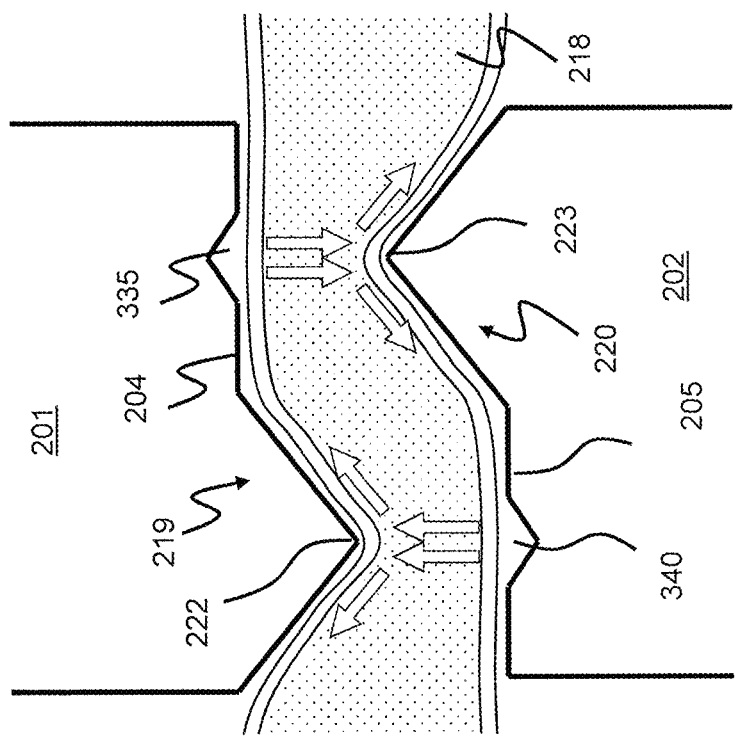
FIG. 10A
FIG. 10B

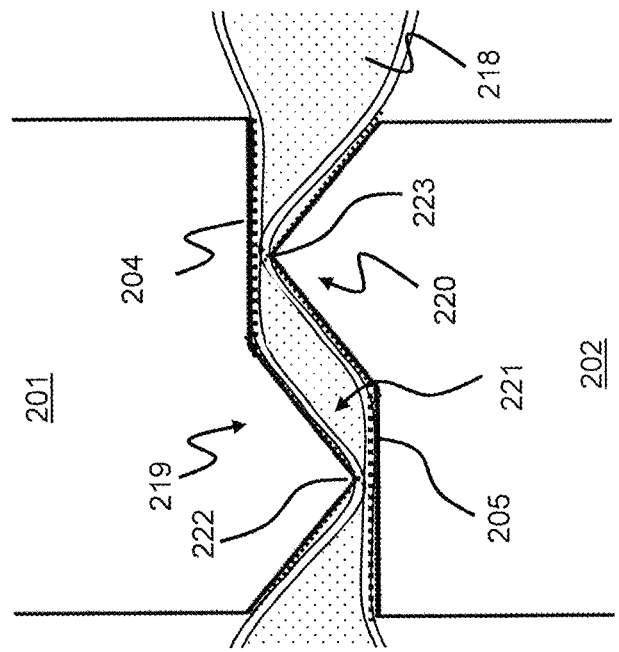
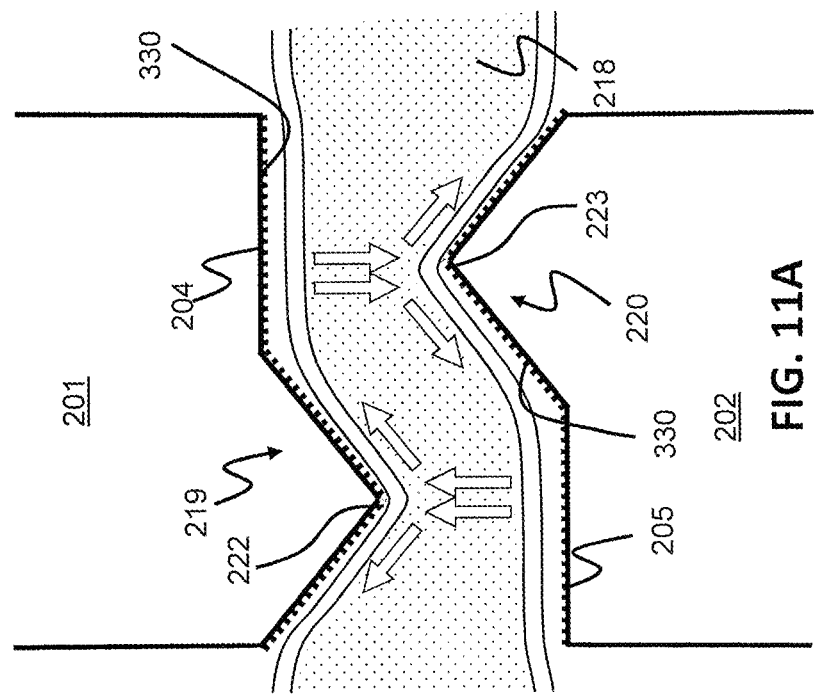

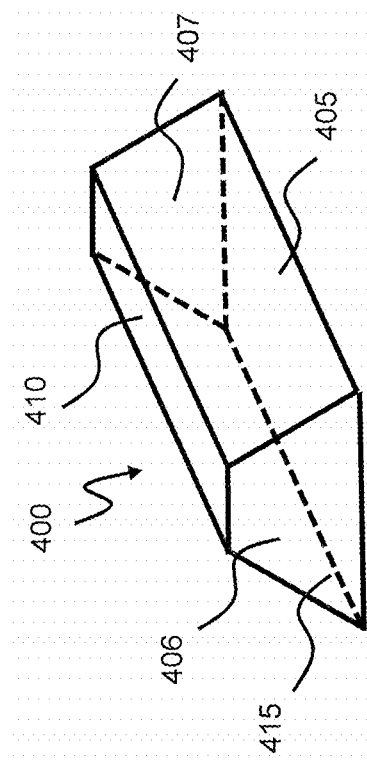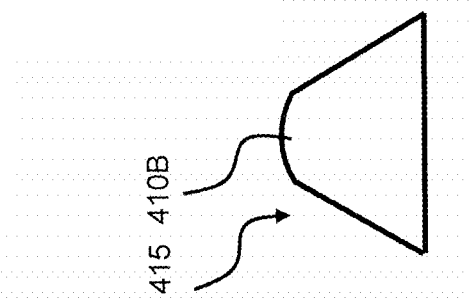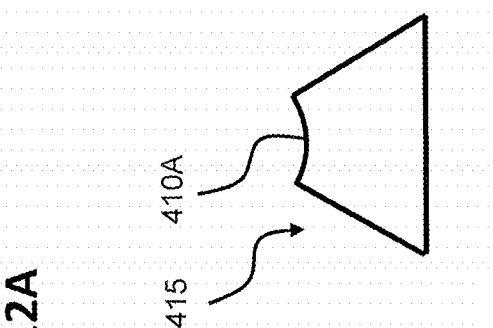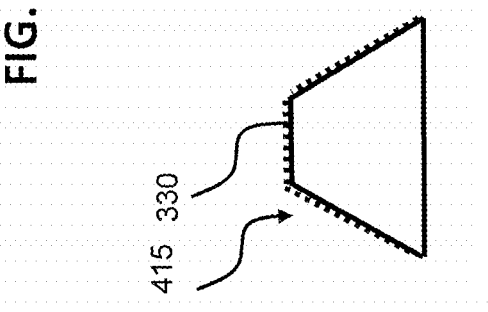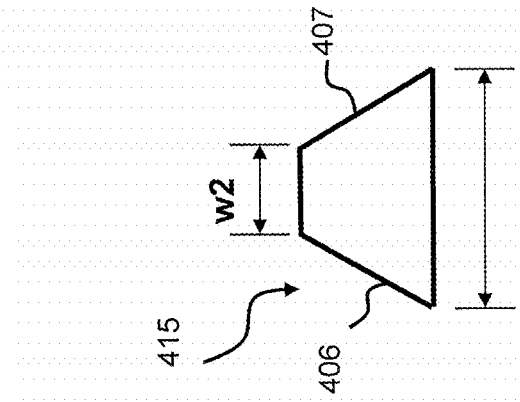

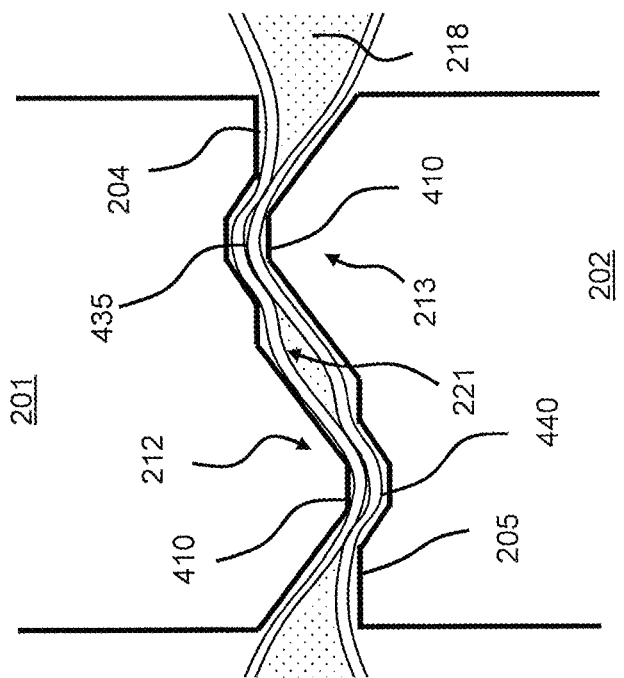
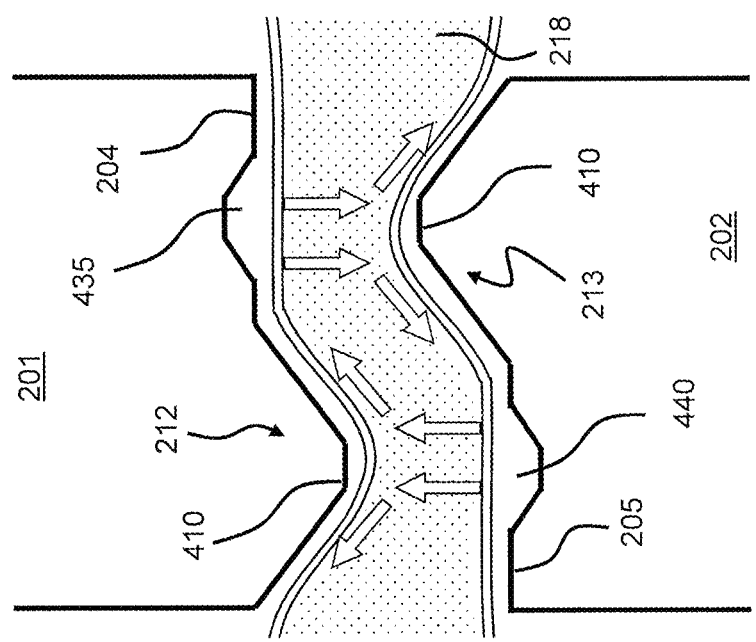
FIG. 14B
FIG. 14A

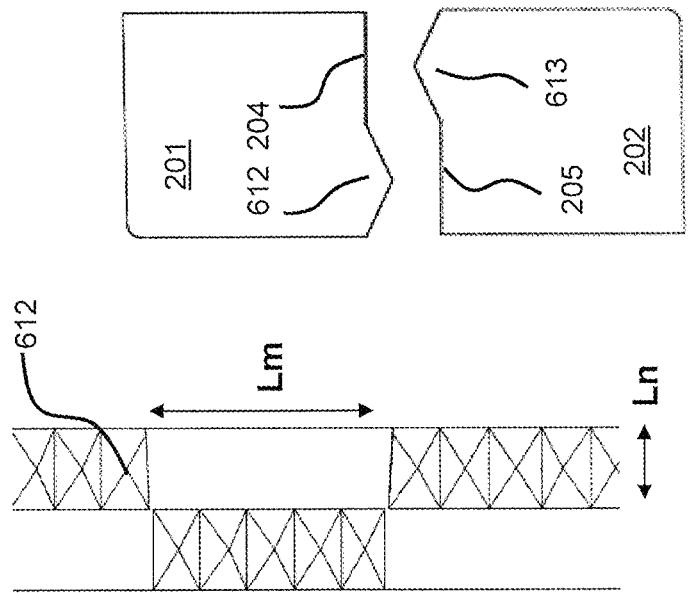
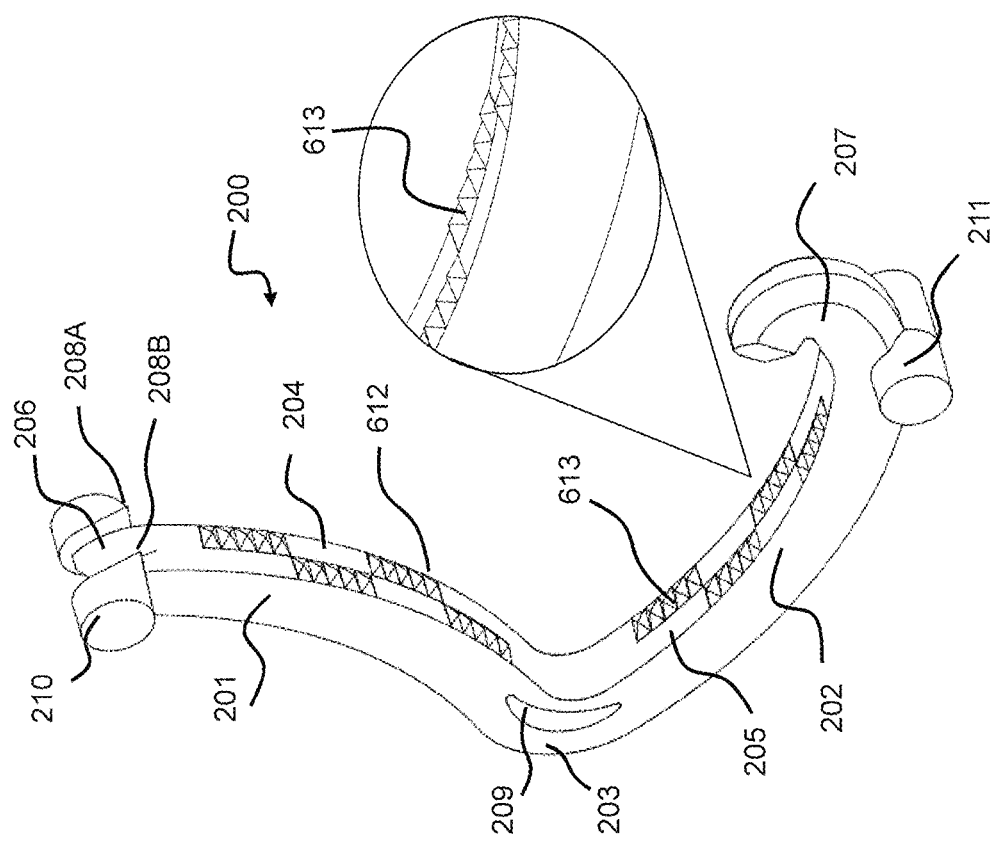

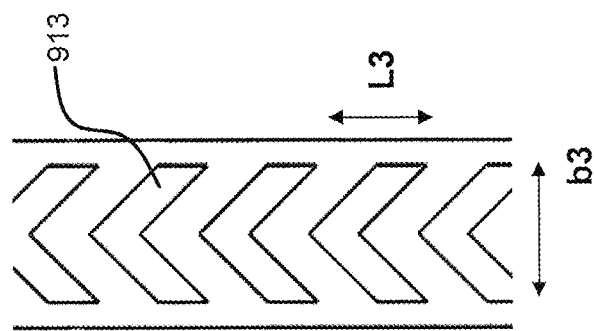
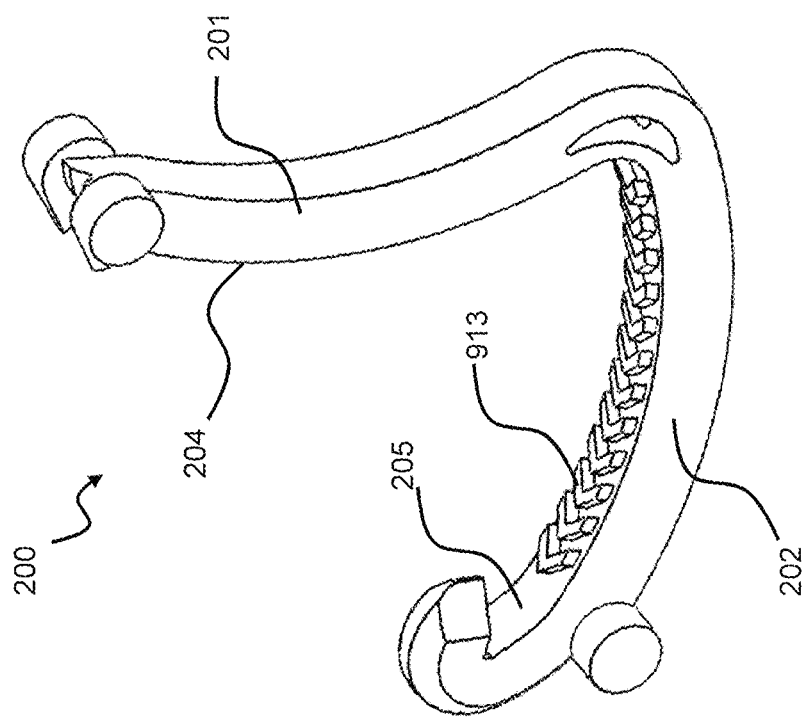

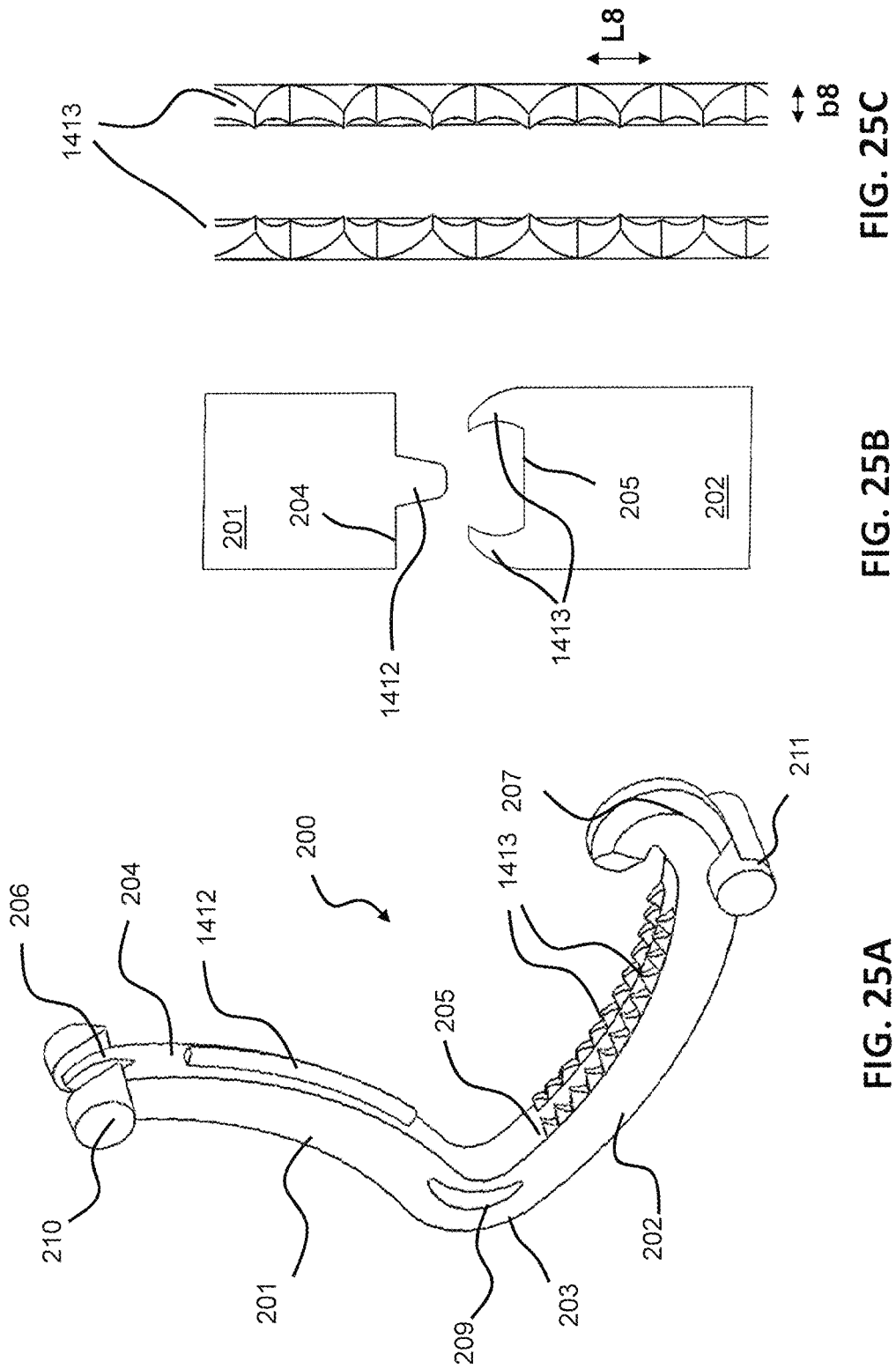

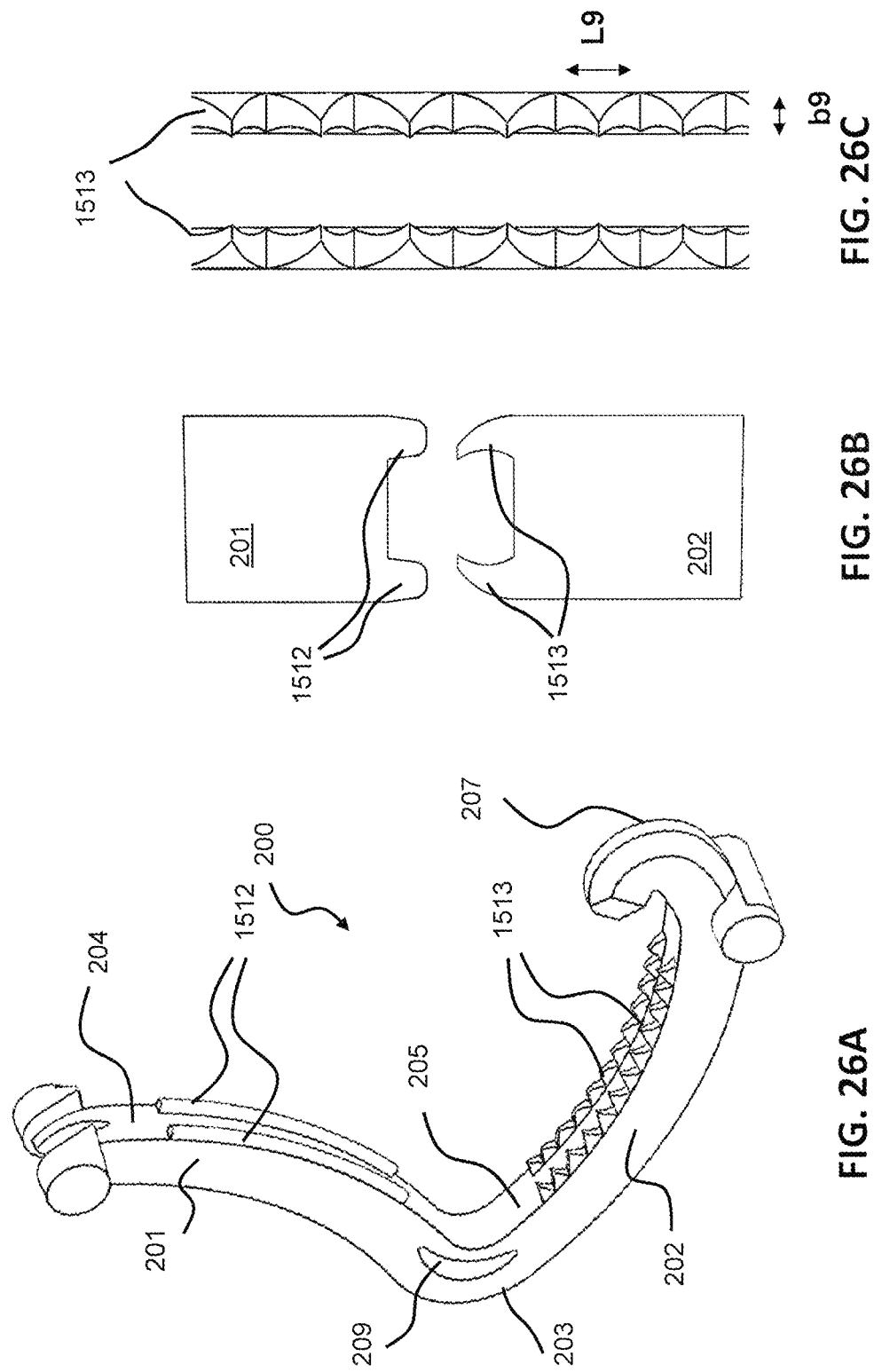

Table 2
| Designs | Max Resistance Force (Newton) | Vessel Breaking Mode (and Vessel Sliding Mode) |
|---|---|---|
| The '846 patent 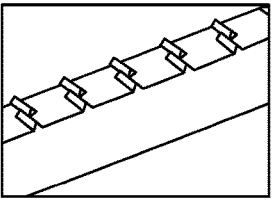 | 17.76±0.38 | 67% (33%) |
| The '454 publication 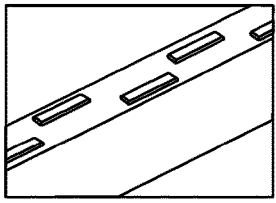 | 4.04±1.24 | 0% (100%) |
| Alternating Gable Structures of Present Structure 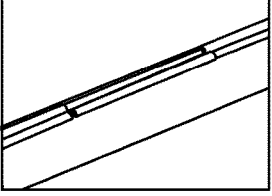 | 21.57±0.75 | 100% (0%) |
*FIG. 29*

ANTI-MIGRATION SURGICAL LIGATION CLIP

CROSS-REFERENCE TO RELATED APPLICATION(S)

This application is a U.S. National Phase Application of International Application No. PCT/US16/37590, filed Jun. 15, 2016, which claims priority to U.S. Provisional Application No. 62/180,532, filed Jun. 16, 2015, the entire contents of all of which are incorporated herein by reference.

TECHNICAL FIELD

The present disclosure relates generally to a surgical clip for the ligation of blood vessels and other tissue structures. More specifically, the present disclosure relates to a surgical clip including protrusions that resist migration or sliding of the surgical clip along the blood vessels or tissue structures.

BACKGROUND

The statements in this section merely provide background information related to the present disclosure and may not constitute prior art.

Many surgical procedures require the ligation of blood vessels to stop the flow of blood. Conventionally, sutures have been used for the ligation of blood vessels using simple suture ties. However, the tedious process and manipulation required to perform the suture operation has led to surgical advances in alternative hemostasis devices. These devices include, but are not limited to, metal ligation clips, polymer non-absorbable ligation clips, absorbable ligation clips, and other devices. Such surgical ligation clips (also referred to as surgical ligating clips or surgical clips) have aided surgeons to reduce the time required for surgery, especially in endoscopic procedures where limited space and visibility reduce the surgeon's ability to perform occlusions and ligation using sutures.

It is important in these procedures that the ligation device deliver a strong, secure, and long lasting hold. In general, a surgical ligation clip is applied with a dedicated medical instrument referred to as a surgical clip applier, a ligating clip applier, or a hemostatic clip applier. The clip applier is depressed firmly by a user to place a ligation clip over the blood vessel or tissue structure.

Surgical clips are distinguished mainly by their materials, such as metal or polymer. Metal clips include stainless steel, Titanium, and Tantalum. Polymer clips are separated into two categories, absorbable and non-absorbable. In recent years, the use of polymer clips has increased, as these devices do not interfere with imaging technologies such as MRI and CAT scans.

The main difference between polymer clips and metal clips lies in their shapes. Most metal clips are symmetric, forming a "V" or "U" shape. An example of one such clip is disclosed in U.S. Pat. No. 5,509,920 to Phillips et al. A major problem plaguing the "V" shaped ligation clips is the uncertain closure. For example, while closing a "V" shaped clip the tissue is effectively pushed away/distally from a hinging point of the clip. This problem was addressed with the "U" shaped design as the distal ends of a clip close first, allowing surgeon control when placing the clip, as described in U.S. Pat. No. 3,363,628 to Ernest et al.

By contrast, many polymer clips are asymmetric. An example of such a polymer surgical clip is disclosed in U.S. Pat. No. 5,062,846 to Oh et al. ("the '846 patent"). The '846 patent describes the polymer surgical clip, as shown in FIG. 1, as having a pair of asymmetric leg members joined at one end by a hinge and being capable of closure at the other end by a latching mechanism.

Although polymer clips have been advanced substantially to improve the ligation of blood vessels and other tissue structures, these devices have not been effective in resisting the migration or sliding of the clips along a blood vessel or tissue structure (e.g., in a longitudinal direction of a blood vessel or tissue structure) after the clips are applied to clamp the blood vessel or tissue structure. The '846 patent discloses a clip including a plurality of protrusions on inner surfaces of leg members to aid in retention of the clamped blood vessel. For example, as shown in FIG. 1, the clip of the '846 patent includes a plurality of protrusions 1302 disposed on an inner surface 20 of a leg member 12, and a plurality of protrusions 1304 disposed on an inner surface 24 of a leg member 14. The protrusions may be ratchet type, wedge shaped, with the wedge opening up towards a hinge portion that joins the leg members 12 and 14.

During operations, the clip of the '846 patent clamps a vessel substantially across the vessel at 90° to the axis of the vessel. The vessel may move or pulse and such movement may cause the clip to become misaligned, thereby degrading its performance or function. The '846 patent purports that the protrusions engage the tissue of the vessel being clamped and assist in preventing the vessel from sliding laterally or longitudinally during or following clip closure.

Although the clip disclosed in the '846 patent may prevent sliding of the clip along a lateral direction of the blood vessel (i.e., sliding in a direction perpendicular to a longitudinal direction of the blood vessel), the protrusions included in the clip disclosed in the '846 patent cannot effectively prevent the migration or sliding of the clip along the vessel (i.e., in the longitudinal direction of the blood vessel). The inventor conducted tests on a prototype clip made according to the '846 patent. The tests show that the prototype clip made according to the '846 patent is ineffective in preventing migration or sliding along the longitudinal direction of the blood vessel. Testing results will be discussed later. A possible reason is because the protrusions of the '846 patent are arranged to extend in a lateral direction of the inner surfaces of the leg members, as shown in FIG. 1. When a blood vessel is clamped, the laterally extending protrusions on the inner surfaces may prevent the clip from moving in the lateral direction of the blood vessel, but cannot provide a resistance force that is sufficient to secure the position of the clip in the longitudinal direction of the blood vessel. As the blood vessel moves or pulses, the clip may start migrating or sliding along the blood vessel.

Many later designs have attempted to improve the migration resistance of the clip disclosed in the '846 patent. However, only limited success has been achieved. Some designs generate an unbalanced load on the vessel or tissue structure while closing, resulting in a lowered migration resistance force and vessel occlusion. Moreover, in an attempt to decrease the migration, many later clips have moved toward conformal closing structure, which includes protruded features that interlock in a perfect manner when the clip is in the closed position. Such designs, however, cause abnormally high and unbalanced forces on the closing/locking mechanism. Additionally, an unbalanced closure force on the inner surface generates unequal forces on the closure mechanism, which results in other issues, such as the clip opening post-surgery, breaking while closing, and damaging tissues.

International application publication WO 2014/142454 A1 to Han ("the '454 publication") introduces a clip design that purports to reduce the migration of the clip in a longitudinal direction of a blood vessel by employing a plurality of pressing protrusions disposed in a longitudinal direction of an inner surface of the clip, as shown in FIG. 2. However, the protrusions disclosed in the '454 publication cannot effectively prevent sliding along a blood vessel. Tests showed that a clip made according to the '454 publication is ineffective in preventing sliding along the longitudinal direction of the blood vessel. Test results will be discussed later.

Therefore, there is a need to provide a surgical ligation clip with protrusion designs that can prevent longitudinal migration along the vessel or tissue structure.

SUMMARY

The present disclosure addresses one or more disadvantages associated with the conventional surgical ligation clips. The disclosed anti-migration surgical ligation clip (or referred to as a surgical clip or a clip) includes a pair of asymmetric leg members joined at their proximal ends by a hinge and being capable of closure at their distal ends by a latching mechanism, similar to the structure described in the '846 patent, which is incorporated herein by reference. The disclosed anti-migration surgical ligation clip further includes a plurality of projections or protrusions with a desirable geometric shape. The protrusions are longitudinally arranged on an inner surface of at least one leg member.

When the disclosed surgical clip is applied upon a blood vessel, the protrusions are approximately perpendicular to the blood vessel. That is, the protrusions that are longitudinally arranged on the inner surface of the at least one leg member securely clamps the blood vessel along the lateral direction of the blood vessel. The longitudinal orientation of the protrusions along the inner surface (or the perpendicular orientation of the protrusions with respect to the longitudinal direction of the blood vessel), and the geometric shape of the projections of the disclosed clip allow for greater resistance to the longitudinal migration along the blood vessel, while providing a balanced closure force. Therefore, the disclosed surgical clip can effectively prevent sliding of the clip in the longitudinal direction of the blood vessel.

In a first aspect of the present disclosure, a surgical clip for ligating a blood vessel or tissue structure is provided. The surgical clip includes a first leg member including a first inner surface and a first plurality of protrusions disposed on the first inner surfaces. The surgical clip also includes a second leg member including a second inner surface and a second plurality of protrusions disposed on the second inner surface. The surgical clip further includes a hinge member joining the first leg member and the second leg member. At least one of the first and second plurality of protrusions includes a gable structure that extends along a longitudinal direction of the first or second inner surface.

In some embodiments of the surgical clip of the first aspect, the gable structure includes a length in the longitudinal direction and a width in a lateral direction of the first or second inner surface, the length being greater than or equal to the width.

In some embodiments of the surgical clip of the first aspect, the first or second inner surface includes a width, and the width of the gable structure is about 30%-70% of the width of the first or second inner surface.

In some embodiments of the surgical clip of the first aspect, the first or second inner surface includes a width, and the width of the gable structure is about 50% of the width of the first or second inner surface.

In some embodiments of the surgical clip of the first aspect, the gable structure has a triangular prism shape that includes a triangular cross section and an apex edge extending along the longitudinal direction.

In some embodiments of the surgical clip of the first aspect, when the first and second leg members are in a closed position, the gable structure faces a portion of the first or second inner surface on an opposite leg member, and the apex edge corresponds to a longitudinal center line of the portion of the first or second inner surface.

In some embodiments of the surgical clip of the first aspect, when the first and second leg members are in a closed position, the gable structure faces a portion of the first or second inner surface on an opposite leg member, and the apex edge corresponds to a longitudinal line located at 30%-70% of a width of the portion of the first or second inner surface.

In some embodiments of the surgical clip of the first aspect, when the first and second leg members are in a closed position, the apex edge is in close proximity to the portion of the first or second inner surface.

In some embodiments of the surgical clip of the first aspect, the portion of the first or second inner surface is a planar surface.

In some embodiments of the surgical clip of the first aspect, when the first and second leg members are in a closed position, the gable structure faces a portion of the first or second inner surface on an opposite leg member, and the portion of the first or second inner surface is a planar surface that includes a recess for receiving the apex edge.

In some embodiments of the surgical clip of the first aspect, when the first and second leg members are in a closed position, the at least one of the first or second plurality of protrusions faces a portion of the first or second inner surface on an opposite leg member.

In some embodiments of the surgical clip of the first aspect, when the first and second leg members are in a closed position, one or more of the first plurality of protrusions are disposed side by side with one or more of the second plurality of protrusions.

In some embodiments of the surgical clip of the first aspect, the first plurality of protrusions is arranged in at least two rows on the first inner surface in the longitudinal direction of the first inner surface, each row including an alternating pattern that includes at least one of the first plurality of protrusions and at least one portion of the first inner surface, and the second plurality of protrusions is arranged in at least two rows on the second inner surface in the longitudinal direction of the second inner surface, each row including an alternating pattern that includes at least one of the second plurality of protrusions and at least one portion of the second inner surface.

In some embodiments of the surgical clip of the first aspect, in the at least two rows on the first or second inner surface, each protrusion included in a first row is disposed side by side in a lateral direction with a portion of the first or second inner surface included in a second row.

In some embodiments of the surgical clip of the first aspect, when the first and second leg members are in a closed position, two protrusions on opposite leg members at corresponding lateral positions are disposed side by side with each other, with each protrusion facing a portion of the first or second inner surface on an opposite leg member.

In some embodiments of the surgical clip of the first aspect, the two protrusions on opposite leg members disposed side by side and the portions of the first and second inner surfaces facing the two protrusions define a cavity between the two protrusions.

In some embodiments of the surgical clip of the first aspect, the cavity has a cross sectional shape of a rhombus or parallelogram type.

In some embodiments of the surgical clip of the first aspect, at least one group of the first plurality of protrusions or the second plurality of protrusions occupies 30% or more of a total area of the first or second inner surface.

In some embodiments of the surgical clip of the first aspect, at least one group of the first plurality of protrusions or the second plurality of protrusions occupies about 30%-50% of a total area of the first or second inner surface.

In some embodiments of the surgical clip of the first aspect, at least one group of the first plurality of protrusions or the second plurality of protrusions is arranged in at least two rows along the longitudinal direction of the first or second inner surface, and a gap between two adjacent protrusions in the longitudinal direction in the at least two rows is about zero.

In some embodiments of the surgical clip of the first aspect, at least one group of the first plurality of protrusions or the second plurality of protrusions is arranged in at least two rows along the longitudinal direction of the first or second inner surface, and a gap between two adjacent protrusions in the longitudinal direction in the at least two rows is about 5%-50% of a length of one of the two adjacent protrusions.

In some embodiments of the surgical clip of the first aspect, the first plurality of protrusions and the second plurality of protrusions have substantially the same dimension.

In some embodiments of the surgical clip of the first aspect, at least two of the first plurality of protrusions have different dimensions.

In some embodiments of the surgical clip of the first aspect, at least two of the second plurality of protrusions have different dimensions.

In some embodiments of the surgical clip of the first aspect, at least one of the first plurality of protrusions has a different dimension compared to at least one of the second plurality of protrusions.

In some embodiments of the surgical clip of the first aspect, the first plurality of protrusions and the second plurality of protrusions have substantially the same shape and same dimension.

In some embodiments of the surgical clip of the first aspect, at least one of the surfaces of the gable structures that form the cavity includes a plurality of barbs.

In some embodiments of the surgical clip of the first aspect, at least one of the surfaces of the gable structures that form the cavity includes a plurality of wavy surfaces.

In some embodiments of the surgical clip of the first aspect, at least one of the surfaces of the gable structures that form the cavity includes a plurality of roughness structures.

In some embodiments of the surgical clip of the first aspect, at least one of the portions of the first and second inner surfaces that form the cavity includes a plurality of barbs.

In some embodiments of the surgical clip of the first aspect, at least one of the surfaces of the gable structures that form the cavity includes a plurality of wavy surfaces.

In some embodiments of the surgical clip of the first aspect, at least one of the surfaces of the gable structures that form the cavity includes a plurality of roughness structures.

In a second aspect of the present disclosure, a surgical clip for ligating a blood vessel or tissue structure is provided. The surgical clip includes a first leg member including a first inner surface and a first plurality of protrusions disposed on the first inner surfaces. The surgical clip also includes a second leg member including a second inner surface and a second plurality of protrusions disposed on the second inner surface. The surgical clip further includes a hinge member joining the first leg member and the second leg member. At least one of the first and second plurality of protrusions includes a structure extending along a longitudinal direction of the first or second inner surface, the structure including a base having a first width in a lateral direction of the first or second inner surface and a top surface having a second width in the lateral direction, the second width being smaller than the first width.

In some embodiments of the surgical clip of the second aspect, the structure includes a trapezoidal cross section having a bottom side with the first width and a top side with the second width.

In some embodiments of the surgical clip of the second aspect, the structure includes a length in the longitudinal direction, the length being greater than or equal to the first width.

In some embodiments of the surgical clip of the second aspect, the first or second inner surface includes a width, and the first width of the structure is about 30%-70% of the width of the first or second inner surface.

In some embodiments of the surgical clip of the second aspect, the first or second inner surface includes a width, and the first width of the structure is about 50% of the width of the first or second inner surface.

In some embodiments of the surgical clip of the second aspect, the second width of the top surface is about 5% to 50% of the first width of the base.

In some embodiments of the surgical clip of the second aspect, the second width of the top surface is about 5% to 20% of the first width of the base.

In some embodiments of the surgical clip of the second aspect, the second width of the top surface is less than 60% of the first width of the base.

In some embodiments of the surgical clip of the second aspect, when the first and second leg members are in a closed position, the top surface faces a portion of the first or second inner surface on an opposite leg member.

In some embodiments of the surgical clip of the second aspect, when the first and second leg members are in a closed position, the top surface is in close proximity to the portion of the first or second inner surface.

In some embodiments of the surgical clip of the second aspect, the portion of the first or second inner surface is a planar surface.

In some embodiments of the surgical clip of the second aspect, when the first and second leg members are in a closed position, the structure faces a portion of the first or second inner surface on an opposite leg member, and the portion of the first or second inner surface is a planar surface that includes a recess for receiving the top surface.

In some embodiments of the surgical clip of the second aspect, when the first and second leg members are in a closed position, the at least one of the first or second plurality of protrusions faces a portion of the first or second inner surface on an opposite leg member.

In some embodiments of the surgical clip of the second aspect, when the first and second leg members are in a closed position, one or more of the first plurality of protrusions are disposed side by side with one or more of the second plurality of protrusions.

In some embodiments of the surgical clip of the second aspect, the first plurality of protrusions is arranged in at least two rows on the first inner surface in the longitudinal direction of the first inner surface, each row including an alternating pattern that includes at least one of the first plurality of protrusions and at least one portion of the first inner surface, and the second plurality of protrusions is arranged in at least two rows on the second inner surface in the longitudinal direction of the second inner surface, each row including an alternating pattern that includes at least one of the second plurality of protrusions and at least one portion of the second inner surface.

In some embodiments of the surgical clip of the second aspect, in the at least two rows on the first or second inner surface, each protrusion included in a first row is disposed side by side in a lateral direction with a portion of the first or second inner surface included in a second row.

In some embodiments of the surgical clip of the second aspect, when the first and second leg members are in a closed position, two protrusions on opposite leg members at corresponding lateral positions are disposed side by side with each other, with each protrusion facing a portion of the first or second inner surface on an opposite leg member.

In some embodiments of the surgical clip of the second aspect, the two protrusions on opposite leg members disposed side by side and the portions of the first and second inner surfaces facing the two protrusions define a cavity between the two protrusions.

In some embodiments of the surgical clip of the second aspect, the cavity has a cross sectional shape of a rhombus or parallelogram type.

In some embodiments of the surgical clip of the second aspect, at least one group of the first plurality of protrusions or the second plurality of protrusions occupies 30% or more of a total area of the first or second inner surface.

In some embodiments of the surgical clip of the second aspect, at least one group of the first plurality of protrusions or the second plurality of protrusions occupies about 30%-50% of a total area of the first or second inner surface.

In some embodiments of the surgical clip of the second aspect, at least one group of the first plurality of protrusions or the second plurality of protrusions is arranged in at least two rows along the longitudinal direction of the first or second inner surface, and a gap between two adjacent protrusions in the longitudinal direction in the at least two rows is about zero.

In some embodiments of the surgical clip of the second aspect, at least one group of the first plurality of protrusions or the second plurality of protrusions is arranged in at least two rows along the longitudinal direction of the first or second inner surface, and a gap between two adjacent protrusions in the longitudinal direction in the at least two rows is about 5%-50% of a length of one of the two adjacent protrusions.

In some embodiments of the surgical clip of the second aspect, the first plurality of protrusions and the second plurality of protrusions have substantially the same dimension.

In some embodiments of the surgical clip of the second aspect, at least two of the first plurality of protrusions have different dimensions.

In some embodiments of the surgical clip of the second aspect, at least two of the second plurality of protrusions have different dimensions.

In some embodiments of the surgical clip of the second aspect, at least one of the first plurality of protrusions has a different dimension compared to at least one of the second plurality of protrusions.

In some embodiments of the surgical clip of the second aspect, the first plurality of protrusions and the second plurality of protrusions have substantially the same shape and same dimension.

In some embodiments of the surgical clip of the second aspect, the top surface includes a planar surface.

In some embodiments of the surgical clip of the second aspect, the top surface includes a convex surface.

In some embodiments of the surgical clip of the second aspect, the top surface includes a concave surface.

In some embodiments of the surgical clip of the second aspect, the top surface includes a wavy surface.

In some embodiments of the surgical clip of the second aspect, the top surface includes a plurality of barbs.

In some embodiments of the surgical clip of the second aspect, the top surface includes a plurality of roughness structures.

In a third aspect of the present disclosure, a surgical clip for ligating a blood vessel or tissue structure is provided. The surgical clip includes a first leg member including a first inner surface and a second leg member including a second inner surface. At least one of the first inner surface and the second inner surface includes a plurality of protrusions. The surgical clip also includes a hinge member joining the first leg member and the second leg member. At least one of the plurality of protrusions includes a gable structure that extends along a longitudinal direction of the first or second inner surface.

In some embodiments of the surgical clip of the third aspect, the first inner surface includes the plurality of protrusions and the second inner surface is a planar surface.

In some embodiments of the surgical clip of the third aspect, the gable structure includes a length in the longitudinal direction and a width in a lateral direction of the first or second inner surface, the length being greater than or equal to the width.

In some embodiments of the surgical clip of the third aspect, the first inner surface includes a width, and the width of the gable structure is about 30%-70% of the width of the first inner surface.

In some embodiments of the surgical clip of the third aspect, the first inner surface includes a width, and the width of the gable structure is about 50% of the width of the first inner surface.

In some embodiments of the surgical clip of the third aspect, the gable structure has a triangular prism shape that includes a triangular cross section and an apex edge extending along the longitudinal direction.

In some embodiments of the surgical clip of the third aspect, when the first and second leg members are in a closed position, the gable structure faces a portion of the second inner surface on the second leg member, and the apex edge corresponds to a longitudinal center line of the portion of the second inner surface.

In some embodiments of the surgical clip of the third aspect, when the first and second leg members are in a closed position, the gable structure faces a portion of the second inner surface on the second leg member, and the apex edge corresponds to a longitudinal line located at 30%-60% of a width of the portion of the second inner surface.

In some embodiments of the surgical clip of the third aspect, when the first and second leg members are in a closed position, the apex edge is in close proximity to the portion of the second inner surface.

In some embodiments of the surgical clip of the third aspect, when the first and second leg members are in a closed position, the gable structure faces a portion of the second inner surface on the second leg member, and the portion of the second inner surface is a planar surface that includes a recess for receiving the apex edge.

In some embodiments of the surgical clip of the third aspect, the plurality of protrusions is arranged in at least two rows on the first inner surface in the longitudinal direction of the first inner surface, each row including an alternating pattern that includes at least one of the plurality of protrusions and at least one portion of the first inner surface.

In some embodiments of the surgical clip of the third aspect, in the at least two rows on the first or second inner surface, each protrusion included in a first row is disposed side by side in a lateral direction with a portion of the first or second inner surface included in a second row.

In some embodiments of the surgical clip of the third aspect, the first plurality of protrusions occupies 30% or more of a total area of the first inner surface.

In some embodiments of the surgical clip of the third aspect, the first plurality of protrusions occupies 30%-50% of a total area of the first inner surface.

In some embodiments of the surgical clip of the third aspect, the first plurality of protrusions is arranged in at least two rows along the longitudinal direction of the first inner surface, and a gap between two adjacent protrusions in the longitudinal direction in the at least two rows is about zero.

In some embodiments of the surgical clip of the third aspect, the plurality of protrusions is arranged in at least two rows along the longitudinal direction of the first inner surface, and a gap between two adjacent protrusions in the longitudinal direction in the at least two rows is about 5%-50% of a length of one of the two adjacent protrusions.

In some embodiments of the surgical clip of the third aspect, the plurality of protrusions has substantially the same shape and same dimension.

In some embodiments of the surgical clip of the third aspect, at least two of the plurality of protrusions have different shapes or different dimensions.

In some embodiments of the surgical clip of the third aspect, at least one side surface of the gable structure includes a plurality of barbs.

In some embodiments of the surgical clip of the third aspect, at least one side surface of the gable structure includes a wavy surface.

In some embodiments of the surgical clip of the third aspect, at least one side surface of the gable structure includes a plurality of roughness structures.

In some embodiments of the surgical clip of the third aspect, at least a portion of the second inner surface includes a plurality of barbs.

In some embodiments of the surgical clip of the third aspect, at least a portion of the second inner surface includes a plurality of wavy surfaces.

In some embodiments of the surgical clip of the third aspect, at least a portion of the second inner surface includes a plurality of roughness structures.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments consistent with the invention and, together with the description, serve to explain the principles of the invention.

FIGS. 4A-4C show top views of an inner surface of the surgical clip shown in FIG. 3A, according to embodiments of the present disclosure.

FIGS. 5A-5B show a perspective view and a top view of an inner surface of a surgical clip, according to another embodiment of the present disclosure.

FIGS. 6A-6B show a perspective view and a top view of an inner surface of a surgical clip, according to another embodiment of the present disclosure.

FIG. 7A schematically illustrates a surgical clip at a closed position without a blood vessel or tissue structure being clamped between the two leg members, according to an embodiment of the present disclosure.

FIG. 7B schematically illustrates a cross sectional view taken along line A-A' in FIG. 7A when the surgical clip is in the closed position, according to an embodiment of the present disclosure.

FIG. 8A is a perspective view of a surgical clip in a closed position clamping a blood vessel, according to an embodiment of the present disclosure.

FIG. 8B is a cross sectional view taken from B-B' line of the surgical clip shown in FIG. 8A, according to an embodiment of the present disclosure.

FIGS. 10A-10B illustrate cross sectional views of a surgical clip in a position approaching the closed position and in the closed position, respectively, according to another embodiment of the present disclosure.

FIGS. 11A-11B illustrate cross sectional views of a surgical clip in a position approaching a closed position, and in the closed position, respectively, according to an embodiment of the present disclosure.

FIGS. 12A-12E illustrate an additional structure and geometric shapes of the protrusions, according to embodiments of the present disclosure.

FIGS. 14A-14B illustrate cross sectional views of a surgical clip in a position approaching a closed position and in the closed position, respectively, according to another embodiment of the present disclosure.

FIGS. 17A-17C show a perspective view, a top view of an inner surface, and a cross sectional view of a surgical clip according to another embodiment of the present disclosure.

FIGS. 20A-20B show a perspective view and a top view of an inner surface of a surgical clip according to another embodiment of the present disclosure.

FIGS. 25A-25C show a perspective view, a cross sectional view, and a top view of an inner surface of a surgical clip according to another embodiment of the present disclosure.

FIGS. 26A-26C show a perspective view, a cross sectional view, and a top view of an inner surface of a surgical clip according to another embodiment of the present disclosure.

FIG. 29 is a Table 2 that shows the migration resistance measured for prototyped protrusions using a simulated blood vessel.

Corresponding reference numerals indicate corresponding parts throughout the several views of drawings.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the invention. Instead, they are merely examples of devices and methods consistent with aspects related to the invention as recited in the appended claims.

The present disclosure relates to a surgical ligation clip (or referred to as a surgical clip or a clip hereinafter) made of, for example, a polymer material, which is configured for ligating blood vessels and/or tissue structures of a human being or animal. The surgical clip is an improvement over a clip disclosed in the '846 patent, which is incorporated herein in its entirety. Similar to the clip disclosed in the '846 patent, the clip disclosed in the present disclosure includes a pair of asymmetric but complimentarily curved legs or leg members, each having a proximal end, a distal end, an inner surface, and an outer surface. The leg members are connected to each other at their proximal ends by a hinge (or hinge member), which may be resilient. The leg members are capable of latching at their distal ends through a pair of latching mechanisms. The inner surfaces of the leg members face each other at a closed position. The term "closed position" refer to both a position in which the leg members are securely latched together, and a position in which the leg members are not securely latched together, but are close to each other with their respective inner surface facing each other.

Figure 1:
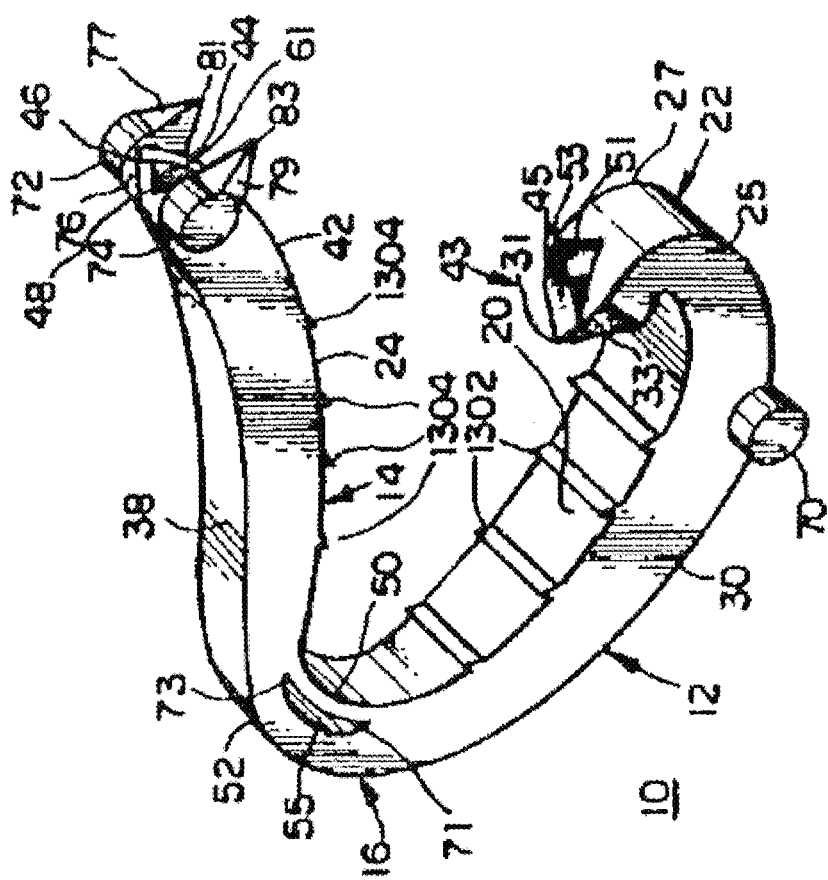
FIG. 1 is a surgical clip disclosed in the '846 patent.

The disclosed surgical ligation clip modifies and improves over the clip disclosed in the '846 patent by replacing sharp protrusions/teeth arranged along a lateral direction of the inner surfaces, as shown in FIG. 1, with protrusions having desirable geometric shapes arranged along a longitudinal direction of the inner surface(s) of the surgical clip. When the surgical clip is at a closing position, the protrusions are oriented perpendicular to the blood vessel being clamped in a lateral direction of the blood vessel. In some embodiments, the desirable geometric shapes help create an array of occlusion cavities with trailing/sloping edges for the blood vessel or tissue structure to be disposed and grasped within the cavities.

Figure 3A:
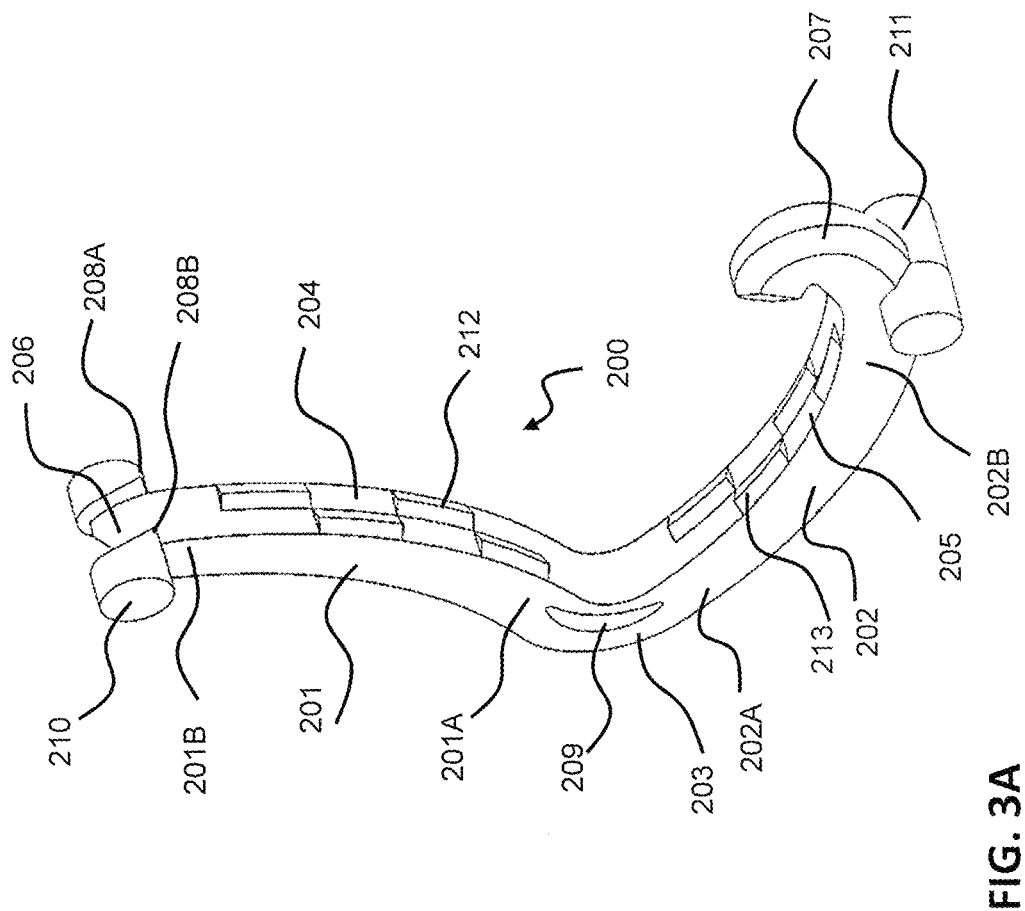
FIG. 3A schematically illustrates a perspective view of a surgical clip according to an embodiment of the present disclosure.

FIG. 3A schematically illustrates a perspective view of a surgical clip according to an exemplary embodiment of the present disclosure. FIG. 3A shows a surgical clip 200 at an open position. Surgical clip 200 may be made of a suitable material, such as metal, polymer, etc. In one embodiment, surgical clip 200 is made of a polymer material. Surgical clip 200 includes a first leg member (or first leg) 201 and a second leg member (or second leg) 202. First leg member 201 includes a proximal end 201A and a distal end 201B. Second leg member 202 includes a proximal end 202A and a distal end 202B. First leg member 201 includes a first inner surface 204. Second leg member 202 includes a second inner surface 205.

First leg member 201 and second leg member 202 are joined together at their proximal ends 201A and 202A by a hinge member 203. Hinge member 203 may be resilient. In some embodiments, hinge member 203 may be replaced with any other suitable connection mechanism. In some embodiments, surgical clip 200 is integrally formed as a single piece by, e.g., injection molding. In such embodiments, first leg member 201, second leg member 202, and hinge member 203 are integrally formed as a single piece. In some embodiments, hinge member 203 may be replaced with a separate hinge mechanism, such as one with a torsional spring or one with two pivoting plates respectively secured to first leg member 201 and second leg member 202.

Surgical clip 200 may include a pair of latch mechanism configured to secure first leg member 201 and second leg member 202 when they are in a closed position. For example, as shown in FIG. 3A, first leg member 201 includes a latch mechanism, such as, a curved slot 206, at distal end 201B. Second leg 202 includes a corresponding latch mechanism, such as a hook 207, at distal end 202B.

Curved slot 206 and hook 207, when latched together, provide a secure closure of first leg member 201 and second leg member 202.

Surgical clip 200 also includes two round boss features 210 and 211 at distal ends 201B and 202B of first leg member 201 and second leg member 202, respectively. Round boss features 210 and 211 are configured to engage surgical clip 200 with a clip applier used to apply surgical clip 200 to blood vessels or tissue structures. Two pointed tips 208A and 208B are integrally formed on both the left and right pieces of round boss feature 210 at distal end 201B. In the embodiment shown in FIG. 3A, pointed tips 208A and 208B are formed at inner ends of both the left and right pieces of round boss feature 210 (i.e., at ends adjacent to inner surface 204 of first leg member 201). Pointed tips 208A and 208B allow for smooth and at least partially aligned closure with hook 207. Pointed tips 208A and 208B also serve the purpose of piercing the blood vessel or tissue structure being clamped to improve the performance of surgical clip 200.

In some embodiment, surgical clip 200 may include only one of the two pointed tips 208A and 208B. In some embodiments, surgical clip 200 may include more than two pointed tips formed on round boss feature 210, such as four, six, etc. In some embodiments, pointed tips 208A and 208B may be formed at other locations on round boss feature 210, such as near a middle portion of both the left and right pieces of round boss feature 210, or at outer surface sides of both the left and right pieces of round boss feature 210.

Surgical clip 200 includes a slot 209 located at hinge member 203. That is, slot 209 is located within the body of hinge member 203. Slot 209 may be a through hole (i.e., a hole completely penetrating through the body of hinge member 203). Alternatively, slot 209 may not completely penetrate through the body of hinge member 203. Slot 209 allows surgical clip 200 to be closed without high stress concentrations, thereby preventing fracture. In the embodiment shown in FIG. 3A, slot 209 includes a crescent moon shape. In some embodiments, slot 209 may include other suitable shapes, such as round shape, oval shape, etc.

The surgical clips disclosed in the present disclosure improves upon the surgical clip disclosed in the prior art by arranging a plurality of protrusions having a desirable geometric shape on at least one of first and second inner surfaces 204 and 205. The protrusions extend along a longitudinal direction of the inner surfaces. When clamping a blood vessel, the protrusions clamp the blood vessel in a lateral direction of the blood vessel. The protrusions may be provided on first inner surface 204, second inner surface 205, or both. The protrusions may be arranged in one row, two rows, three rows, or any suitable number of rows. The protrusions may be arranged in other patterns other than rows. The protrusions may be integrally formed on the inner surface of at least one of the leg members 201 and 202, such as by injection molding. The protrusions may extrude from the inner surfaces.

For example, comparing surgical clip 200 shown in FIG. 3A with the surgical clip disclosed in the '846 patent shown in FIG. 1, surgical clip 200 modifies and improves upon the clip of the '846 patent by including a plurality of protrusions having a desirable shape on first and second inner surfaces 204 and 205. The protrusions arranged on the first and second inner surfaces 204 and 205 extend in a longitudinal direction of the first and second inner surfaces 204 and 205. The protrusions arranged on the first and second inner surfaces 204 and 205 complement each other when surgical clip 200 is in a closed position.

As shown in FIG. 3A, first inner surface 204 is provided with a first plurality of protrusions 212, and second inner surface 205 is provided with a second plurality of protrusions 213. At least one of the first and second plurality of protrusions 212 and 213 includes desirable shape, such as a gable structure. Examples of the gable structure are shown in FIGS. 3B-3I and discussed below. In some embodiments, at least one of the first plurality of protrusions 212 includes a gable structure. For example, all of the first plurality of protrusions 212 may include a gable structure. As another example, at least one of the first plurality of protrusions 212 may include a gable structure, while the rest of the first plurality of protrusions 212 may include one or more structures that are different from the gable structure. In some embodiments, at least one of the second plurality of protrusions 213 includes a gable structure. For example, all of the second plurality of protrusions 213 may include a gable structure. As another example, at least one of the second plurality of protrusions 213 may include a gable structure, while the rest of the second plurality of protrusions 213 may include one or more structures that are different from the gable structure.

FIGS. 3B-3I show examples of a gable structure, according to embodiments of the present disclosure. The gable structure shown in FIGS. 3B-3I is applicable to at least one of the first plurality of protrusions 212, and/or at least one of the second plurality of protrusions 213. In some embodiments, all protrusions 212 and 213 include the gable structure. In some embodiments, all protrusions 212 include the gable structure, while all protrusions 213 include another structure disclosed herein that is different from the gable structure. In some embodiments, at least one of protrusions 212 includes the gable structure, while the rest of protrusions 212 have a structure disclosed herein that is different from the gable structure shown in FIGS. 3B-3I. In some embodiments all protrusions 213 include the gable structure, while all protrusions 212 include another structure disclosed herein that is different from the gable structure. In some embodiments, at least one of protrusions 213 includes the gable structure, while the rest of protrusions 213 have a structure disclosed herein that is different from the gable structure shown in FIGS. 3B-3I.

Figure 3B:
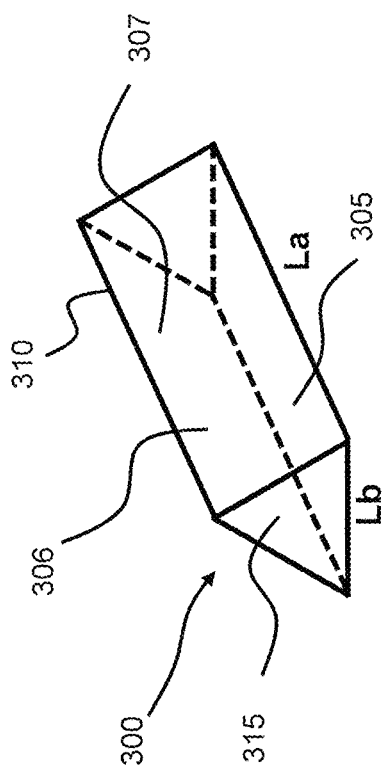
FIG. 3B schematically illustrates a perspective view of a gable structure according to an embodiment of the present disclosure.

FIG. 3B schematically shows a perspective view of a gable structure 300, according to an embodiment of the present disclosure. Gable structure 300 includes a base 305, a first (left) longitudinal side surface 306, a second (right) longitudinal side surface 307, a top portion 310, and a cross section 315. Top portion 310 is also referred to as an apex edge 310. Gable structure 300 includes a length La in a longitudinal direction, and a width Lb in a lateral direction.

As shown in FIG. 3B, gable structure 300 includes a triangular prism shape having an extended body. Base 305 of gable structure 300 is in contact with first inner surface 204 and/or second inner surface 205 on which gable structure 300 is disposed (or from which gable structure 300 protrudes). In some embodiments, when gable structure 300 is integrally formed with first leg member 201 and/or second leg member 202 on the first inner surface 204 and/or second inner surface 205, base 305 is integral with the first inner surface 204 and/or second inner surface 205.

Figure 3F:
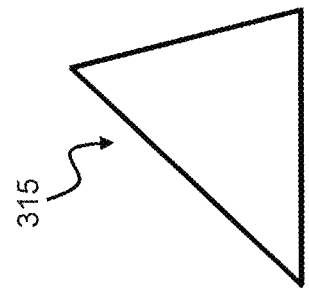
FIGS. 3C-3I show shapes of the cross section of the gable structure, according to embodiments of the present disclosure.
Figure 3E:
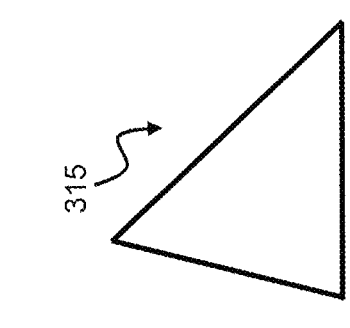
Figure 3D:
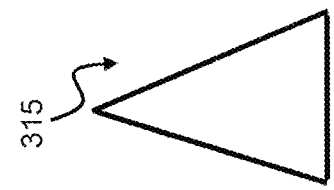
Figure 3C:
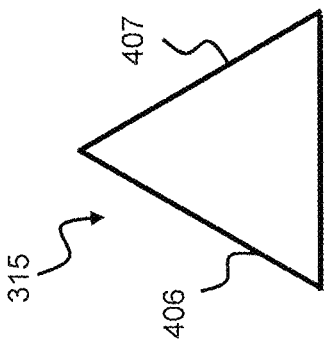

Cross section 315 may include any suitable triangle type shape. A triangle type shape includes a triangle shape and any shape that substantially resemble a triangle. FIGS. 3C-3H show different shapes of cross section 315. Cross section 315 may be an equilateral triangle, as shown in FIG. 3C, an isosceles triangle (acute or obtuse, although only acute is shown), as shown in FIG. 3D, a scalene triangle with the peak point located to the left of a center point on the bottom side of the triangle, as shown in FIG. 3E, or a scalene triangle with the peak point located to the right of the center point on the bottom side of the triangle, as shown in FIG. 3F. Cross section 315 may be other suitable triangles, such as isosceles and right triangle, scalene and acute triangle, scalene and obtuse triangle, scalene and right triangle, etc.

Figure 3H:
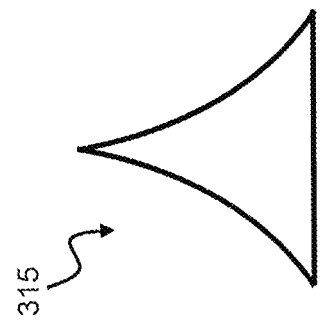
Figure 3I:
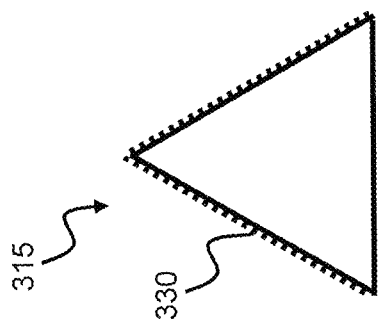
Figure 3G:
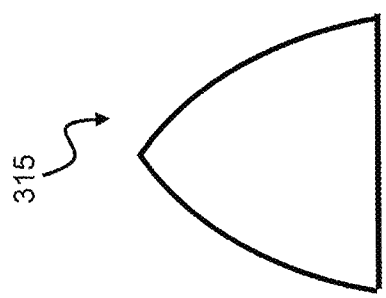

FIGS. 3G-3H show examples of cross section 315 in a triangle type shape with curved sides, according to embodiments of the present disclosure. For example, cross section 315 may have a shape that substantially resembles a triangle, with one or both of the side lines being not straight. For example, one or both of the side lines of cross section 315 may be curved. FIG. 3G shows convex curves for the left and right side lines of cross section 315. FIG. 3H shows concave curves for the left and right side lines of cross section 315. Although both side lines are shown as curved lines, in some embodiments, one side line of cross section 315 may be curved, and the other side line of cross section 315 may be straight. Cross section 315 of any other triangular shapes, such as those shown in FIGS. 3D-3F, may also be modified to include one or more curved side lines, similar to those shown in FIGS. 3G-3H.

Curved side lines in cross section 315 correspond to curved first and second longitudinal side surfaces 306 and 307 of gable structure 300. For example, when cross section 315 of gable structure 300 includes the convex sides shown in FIG. 3G, first and second longitudinal side surfaces 306 and 307 of gable structure 300 are convex surfaces. As another example, when cross section 315 of gable structure 300 includes the concave sides shown in FIG. 3H, first and second longitudinal side surfaces 306 and 307 of gable structure 300 are concave surfaces.

In some embodiments, when only one side (e.g., the left or the right side) of cross section 315 is curved, only one of the first and second longitudinal side surfaces 306 and 307 of gable structure 300 is a curved surface. Although convex and concave sides are shown in FIGS. 3G-3H for illustrative purposes, cross section 315 may include one or more curved sides of other shapes, such as a combination of convex and concave lines (e.g., one or more wavy sides), which correspond to wavy longitudinal side surface 306 and/or 307.

While complementary gable-shaped protrusions 212 and 213 are illustrated in FIGS. 3A and 3B, protrusions 212 and 213 may have various other geometric shapes to impede migration and increase the vessel occlusion force while providing the balanced closure and superior vessel occlusion. Features such as barbs and surface roughness, may also be included in various embodiments of the present disclosure to resist migration and enhance vessel occlusion.

For example, at least one of the two longitudinal side surfaces 306 and 307 of gable structure 300 may include one or more roughness structures. The term "roughness structure" includes any suitable small structures that increase the roughness of a surface, such as bumps, barbs, recesses, projections, patterns, spikes, uneven surfaces such as wavy surfaces, etc. The roughness structures disposed on a surface (e.g., a surface of the protrusion or an inner surface) may increase the grasping force of surgical clip 200 by increasing the friction between the surface and the blood vessel or tissue structure that is being clamped.

FIG. 3I shows an example cross section 315 of gable structure 300 with roughness structures disposed on the left and right sides, according to an embodiment of the present disclosure. In other words, first and second longitudinal side surfaces 306 and 307 of gable structure 300 include roughness structures 330. Roughness structures 330 can be any one of the roughness structures discussed above. Although roughness structures 330 are shown based on the embodiment of cross section 315 shown in FIG. 3C, roughness structures 330 can be included in any other embodiments of cross section 315, such as those shown in FIGS. 3D-3H. In other words, longitudinal side surfaces 306 and 307 of gable structure 300 having cross section 315 of other shapes shown in FIGS. 3D-3H may also include roughness structures 330.

In some embodiments, protrusions having gable structure 300 may be provided on first leg member 201, second leg member 202, or both. Protrusions provided on both of first leg member 201 and second leg member 202 may have the same or different shapes and/or dimensions. For example, protrusions 212 and 213 may have the same shape and dimension. In some embodiments, protrusions 212 provided on first leg member 201 may have a first shape and a first dimension, while protrusions 213 provided on second leg member 202 may have a second shape (different from the first shape) and a second dimension (different from the first dimension). In some embodiments, protrusions provided on the same leg member (e.g., on first leg member 201 or second leg member 202) may have the same shape and same dimension. For example, protrusions 212 included on first inner surface 204 may have the same shape and/or dimension. Protrusions 213 included on second inner surface 205 may have the same shape and/or dimension. In some embodiments, protrusions provided on the same leg member may include a mixture of protrusions having different shapes and/or different dimensions. For example, at least one of protrusions 212 may have a shape and/or dimension that is different from the rest of protrusions 212. At least one of protrusions 213 may have a shape and/or dimension that is different from the rest of protrusions 213.

Referring back to FIG. 3A, first plurality of protrusions 212 having gable structure 300 is disposed on first inner surface 204 at locations where protrusions are absent at corresponding locations on second inner surface 205 on opposite second leg member 202. Likewise, second plurality of protrusions 213 having gable structure 300 is disposed on second inner surface 205 at locations where protrusions are absent at corresponding locations on first inner surface 204 on opposite first leg member 201.

FIGS. 4A-4C are top views of an inner surface of a leg member shown in FIG. 3A, illustrating the orientation and arrangement of the protrusions, according to embodiments of the present disclosure. For illustrative purposes, the top views shown in FIGS. 4A-4C are top views of first inner surface 204 of first leg member 201 shown in FIG. 3A, on which first plurality of protrusions 212 is provided. It is understood that the tops views shown in FIGS. 4A-4C may be top views of second inner surface 205 of second leg member 202 shown in FIG. 3A, on which second plurality of protrusions 213 is provided. Top view of second inner surface 205 may be complementary to the top view of first inner surface 204. The protrusions shown in FIGS. 4A-4C may include a gable structure shown in FIGS. 3B-3I.

As shown in FIG. 4A and FIG. 3A, first plurality of protrusions 212 is disposed on first inner surface 204 in the longitudinal direction of first inner surface 204. Protrusions 212 are arranged in two rows, although in other embodiments, they may be arranged in one row, three rows, four rows, or any other suitable number of rows. The protrusions 212 may have the same shape and same dimension. Each row includes an alternating pattern that has at least one of the first plurality of protrusions and at least one portion of the first inner surface 204. As shown in FIG. 4A, the left row includes an alternating pattern that has two protrusions 212 and a portion of first inner surface 204 located between the two protrusions 212. It is understood that the alternating pattern may be repeated in the left row to include more protrusions and more portions of first inner surface 204. The right row includes an alternating pattern that has one protrusion 212 located between two portions of first inner surface 204. It is understood that the alternating pattern may be repeated in the right row to include more protrusions and more portions of first inner surface 204.

As shown in FIG. 3A and FIG. 4A, each protrusion 212 includes a length La and a width Lb. The length La is greater than or equal to the width Lb. In some embodiments, the ratio between length La and width Lb is greater than 1.0, such as greater than 5.0, greater than 10.0, greater than 30.0, greater than 50.0, greater than 100.0, or greater than any suitable number. In the two rows of protrusions 212 shown in FIG. 4A, a gap between two adjacent protrusions 212 in the two rows is about zero, although in other embodiments, the gap may be greater than zero. In the two rows shown in FIG. 4A, each protrusion 212 is disposed side by side in a lateral direction of first leg member 212 (or first inner surface 204) with a portion of the first inner surface 204 (e.g., a planar portion of the first inner surface 204). When surgical clip 200 is in a closed position, each protrusion 212 shown in FIG. 4A faces a portion of second inner surface 205 on second leg member 202, where protrusion 213 is absent. In the closed position, at least one portion of first inner surface 204, where protrusion 212 is absent, faces a protrusion 213 on second leg member 202. In the embodiment shown in FIG. 4A, a gap between two protrusions 212 in different rows in the lateral direction is about zero, although in other embodiments, the gap in the lateral direction may be greater than zero.

In the embodiment shown in FIG. 4A, the width Lb of protrusion 212 is about one half of a width Ls of first inner surface 204. The width Lb of protrusion 212 may be any suitable percentage of the width Ls of first inner surface 204, such as between 30%-70% of width Ls. In the embodiment shown in FIG. 4A, a protrusion 212 occupies about 50% of the width of first inner surface 204 (i.e., Lb is 50% of Ls), and the other 50% of the width of first inner surface 204 does not include a protrusion. That is, the portion of the first inner surface 204 that is disposed side by side with a protrusion 212 has the same width Lb as the protrusion 212, and the same length La as the protrusion 212. In some embodiments, the longitudinal length of the portion of inner surface 204 may be greater than the length of protrusion 212.

Although protrusions 212 are shown in FIG. 4A as having the same length, in some embodiments, they may have different lengths. For example, at least two of the protrusions 212 may have different lengths. In one embodiment, protrusions 212 in a first row may all have a same first length, and protrusions 212 in a second row may all have a same second length. The first length may be different from the second length. In some embodiments, protrusions in the same row may have different lengths. In some embodiments, at least one of the protrusions 212 may have a length that is greater than or equal to its width. In some embodiments, at least one of the protrusions 212 may have a length that is less than its width.

FIG. 4B shows another top view of first inner surface 204 of first leg member 201, illustrating orientation and arrangement of protrusions on first inner surface 204 according to another embodiment of the present disclosure. As shown in FIG. 4B, protrusions 212 provided on first inner surface 204 may have different widths. In some embodiments, at least two protrusions disposed on first inner surface 204 may have different widths.

For example, the protrusions 212 may be arranged in two rows. Protrusions in each row may have the same shape and dimension (e.g., width and length), while protrusions in different rows may have different dimensions (e.g., width and/or length). A first row (left row) includes an alternating pattern having at least one protrusion 212A with a first width Lb1 and at least one first portion 204A of first inner surface 204. The alternating pattern in the first row shown in FIG. 4B may be repeated to include more than one protrusion 212A. A second row (right row) includes an alternating pattern having at least one protrusion 212B with a second width Lb2 and at least one second portion 204B of first inner surface 204. The alternating pattern in the second row shown in FIG. 4B may be repeated to include more than one second portion 204B of first inner surface 204.

In the embodiment shown in FIG. 4B, first width Lb1 of protrusions 212A is greater than second width Lb2 of protrusions 212B. First portion 204A of first inner surface 204 has the same width as protrusion 212A, i.e., Lb1. Second portion 204B of first inner surface 204 has the same width as protrusion 212B, i.e., Lb2. So, the first portion 204A of first inner surface 204 has a width greater than the second portion 204B of first inner surface 204. The length of protrusion 212A may be the same as or different from the length of protrusions 212B.

First width Lb1 of protrusion 212A may be about 60%-80% of the width Ls of first inner surface 204. For example, first width Lb1 may be about 60% of the width Ls of first inner surface 204. As another example, first width Lb1 may be about 70% of the width Ls of first inner surface 204. Second width Lb2 may be about 20%-40% of the width Ls of first inner surface 204. For example, second width Lb2 may be about 20%, 30%, or 40% of the width Ls.

In some embodiments, the ratio between Lb1 (width of protrusion 212A or first portion 204A) and Lb2 (width of protrusion 212B or second portion 204B) may be 1.5, 2.0, 2.5, 3.0, 3.5, 4.0, or other suitable numbers. Except for the widths, other features discussed above in connection with the embodiment shown in FIG. 4A are also applicable to the embodiment shown in FIG. 4B. For example, a gap between two adjacent protrusions in the longitudinal direction in two different rows shown in FIG. 4B is about zero.

The narrower protrusion 212B may include a length La1 and a width Lb2. Length La1 may be greater than width Lb2. Like the ratio between length La and width Lb in FIG. 4A, the ratio between the length La1 and the width Lb2 may be greater than 1.0, such as greater than 5.0, greater than 10.0, greater than 30.0, greater than 50.0, greater than 100.0, or greater than any other suitable number. Length of the wider protrusion 212A may be the same as La1, or may be different. The ratio between the length of the wider protrusion 212A and its width Lb1 may be greater than 1.0, 2.0, 3.0, or any other suitable number. The ratio between the length of the wider protrusion 212A and its width Lb1 may be less than the ratio between the length La1 of the narrower protrusion 212B and its width Lb2.

FIG. 4C shows another top view of first inner surface 204 of first leg member 201, illustrating orientation and arrangement, of protrusions on first inner surface 204 according to another embodiment of the present disclosure. As shown in FIG. 4C, protrusions 212C may be arranged in two rows, although in other embodiments, they may be arranged in one row, three rows, four rows, or any other suitable number of rows. Protrusions 212C may include the same shape and same dimension. For example, as shown in FIG. 4C, each protrusion 212C includes a width Lb3.

Comparing FIG. 4C and FIG. 4A, in the embodiment shown in FIG. 4C, protrusions 212C in different rows are separated apart by a gap Lc in the lateral direction of first inner surface 204. In the embodiment shown in FIG. 4C, the portion of first inner surface 204 disposed side by side with a protrusion 212C has a width Lp that is greater than the width Lb3 of protrusion 212C. In some embodiments, a ratio between the width Lp of the portion of first inner surface 204 on which a protrusion is absent and the width Lb3 of protrusion 212C is about 1.5, 2.0, 2.5, 3.0, 3.5, 4.0, or any other suitable numbers. The length of each protrusion 212C may be the same, i.e., La2, or at least one of the protrusions 212C may have a length La2. The ratio between the length of protrusion 212C and its width Lb3 may be greater than 1.0, such as greater than 5.0, greater than 10.0, greater than 30.0, greater than 50.0, greater than 100.0, or greater than any suitable number.

As shown in FIG. 4C, protrusions 212C in two adjacent rows are separated in the lateral direction of first inner surface 204 by a gap Lc. The gap Lc may be any suitable percentage of the width Ls of first inner surface 204. For example, the ratio between gap Lc and width Ls may be between 10%-40%, such as 10%, 20%, 30%, or 40%. In some embodiments, the ratio between gap Lc and width Ls is about 30%. For example, in some embodiments, the width Lb3 of each protrusion 212C may be about ⅓ of the width Ls of first inner surface 204, and the gap Lc may be ⅓ of the width Ls. Although as shown in FIG. 4C, a gap between two adjacent protrusions 212C in the longitudinal direction of first inner surface 204 is about zero, the gap in the longitudinal direction may be greater than zero.

FIG. 5A schematically shows a perspective view of surgical clip 200, according to another embodiment of the present disclosure. FIG. 5B shows a top view of first inner surface 204 shown in FIG. 5A. Surgical clip 200 of this embodiment is similar to that shown in FIG. 3A, except that a gap between two adjacent protrusions in different rows in the longitudinal direction of first inner surface 204 is greater than zero, i.e., Ld>0. The gap Ld between two adjacent protrusions may be within a range of 10%-100% of the length La of the protrusions. For example, Ld may be 10% of La, 20% of La, 30% of La, etc. The descriptions of features included in the embodiment shown in FIGS. 5A and 5B are similar to those of the embodiments shown in FIGS. 3A-4C, except for the non-zero gap, and hence are not repeated. It is understood that the features included in the embodiments shown in FIGS. 3A-4C may also be included in the embodiment shown in FIGS. 5A-5B. The descriptions of such features are not repeated.

FIG. 6A schematically shows a perspective view of surgical clip 200, according to another embodiment of the present disclosure. FIG. 6B shows a top view of first inner surface 204 shown in FIG. 5A. Surgical clip 200 shown in FIGS. 6A and 6B is similar to that shown in FIGS. 3A and 3B, except that three rows of protrusions are provided on first inner surface 204 and second inner surface 205. Thus, the descriptions of similar elements shown in FIGS. 3A-3B are also applicable to FIGS. 6A-6B, and hence are not repeated. In addition, at least one of protrusions 212 and 213 shown in FIGS. 6A-6B may include the gable structure described above in connection with FIGS. 3B-3I. Thus, the above descriptions of the gable structure may also be applicable to at least one of protrusions 212 and 213 shown in FIG. 6A-6B, and hence are not repeated.

Furthermore, the top view of protrusions 212 shown in FIG. 6B is similar to the arrangement of protrusions shown in FIG. 4A except that an additional row is added to the embodiment shown in FIG. 4A. Hence, the descriptions of FIG. 4A are also applicable to FIG. 6A, and are not repeated.

Moreover, protrusions 212 provided on first inner surface 204 in the embodiment shown in FIG. 6A may have top views similar to those shown in FIGS. 4B-4C, except that an additional row of protrusions is added to the embodiments shown in FIGS. 4B-4C. For example, based on the embodiment shown in FIG. 4B, an additional row of alternating pattern having the wider protrusion (with width Lb1) may be added next to the wider row (with width Lb1) or the narrower row (with width Lb2). As another example, based on the embodiment shown in FIG. 4C, an additional row of alternating pattern having width Lb3 may be added next to the row having the width Lb3, or next to the row having the width Lp. As a further example, based on the embodiment shown in FIG. 4C, an additional row of alternating pattern having width Lp may be added next to the row having width Lp, or next to the row having the width Lb3.

In addition, the three-row embodiment shown in FIGS. 6A-6B may be arranged in a manner similar to those shown in FIGS. 5A-5B, such that a gap between two adjacent protrusions 212 (or 213) in the longitudinal direction in different rows is greater than zero. Thus, the above descriptions of FIGS. 5A-5B are also applicable to this variation of the three-row embodiment shown in FIGS. 6A-6B, and hence are not repeated.

Although a two-row embodiment (FIG. 3A) and a three-row embodiment (FIG. 6A) are shown for illustrative purposes, protrusions 212 and 213 may be arranged in one row, four rows, five rows, or any other suitable number of rows. In addition, although both first and second inner surfaces 204 and 205 are shown in FIG. 6A as being provided with protrusions 212 and 213, one of the first and second inner surfaces 204 and 205 may not be provided with protrusions. For example, one of first and second inner surfaces 204 and 205 may include a planar surface without protrusions, or a planar surface having roughness structures but without protrusions. It is understood that the features included in the embodiments shown in FIGS. 3A-5B may also be included in the embodiment shown in FIGS. 6A-6B. Hence the descriptions of such features are not repeated.

The descriptions of the shape and/or dimension of the protrusions included in the embodiments shown in FIG. 3A-5B are also applicable to the embodiment shown in FIGS. 6A-6B. For example, in the three-row embodiment show in FIG. 6A, protrusions included in a row may have the same shape and/or dimension. For example, all of the protrusions 212 (or 213) may include the same shape and/or dimension. In one embodiment, as shown in FIGS. 6A and 6B, all of the protrusions 212 (or 213) include a width Lb that is ⅓ of the width Ls of first inner surface 204. In some embodiments, protrusions included in different rows may include different shape and/or dimension. For example, in one embodiment, at least two protrusions included in different two rows may include different shapes, different dimensions, or both.

FIG. 7A schematically illustrates surgical clip 200 of FIG. 3A at a closed position without a blood vessel or tissue structure being clamped between the two leg members, according to an embodiment of the present disclosure. FIG. 7B schematically illustrates a cross sectional view taken along line A-A' in FIG. 7A when surgical clip 200 is in the closed position.

As used herein, the term "closed position" generally refers to any position that two legs of the surgical ligation clip are closely facing each other, which includes the completely closed position (with the latching mechanism 206 and 207 engaged with each other) and any position that is nearly completely closed (without the latching mechanism 206 and 207 engaged with each other).

The cross sectional view shown in FIG. 7B is based on the embodiment shown in FIG. 3A, in which protrusions 212 are provided on first inner surface 204 and protrusions 213 are provided on second inner surface 205. FIGS. 7A-7B show second leg member 202 on top of first leg member 201. As shown in FIG. 7B, each protrusion 212 provided on first inner surface 204 includes a gable structure 219, and each protrusion 213 provided on second inner surface 205 includes a gable structure 220. Protrusion 212 and protrusion 213 are disposed side by side with each other.

As described above in connection with FIGS. 3A-3B, and as shown in FIG. 7B, each of gable structures 219 and 220 includes a triangular cross section and two sloped or slant side surfaces extending along the longitudinal direction of first inner surface 204 and second inner surface 205, respectively. The slant side surfaces form a convex shape in each gable structure 219 and 220, such as a V shape (or a reverse V shape). Gable structure 219 includes an apex edge 222 (or peak 222), which is a common edge line of the two slant side surfaces of gable structure 219. Apex edge 222 extends along the longitudinal direction of first inner surface 204. Likewise, gable structure 220 includes an apex edge 223 (or peak 223), which is a common edge line of the two slant side surfaces of gable structure 220. Apex edge 223 extends along the longitudinal direction of second inner surface 205.

In the closed position, as shown in FIG. 7B, gable structure 219 faces a portion of second inner surface 205 on opposite second leg member 202, and gable structure 220 faces a portion of first inner surface 204 on opposite first leg member 201. Specifically, as shown in FIG. 7B, the slant side surfaces and apex edge 222 of gable structure 219 on first leg member 201 face a portion of second inner surface 205 on the opposite leg member 202, and the slant side surfaces and apex edge 223 of gable structure 220 on second leg member 202 face a portion of first inner surface 204. In the embodiment shown in FIG. 7B, the portion of second inner surface 205 is a planar surface. In some embodiments, the entire second inner surface 205 may be a planar surface. Likewise, in the embodiment shown in FIG. 7B, the portion of first inner surface 204 is a planar surface. In some embodiments, the entire first inner surface 204 may be a planar surface.

At the closed position, apex edge 222 is in close proximity to the portion of second inner surface 205 that faces apex edge 222. In some embodiments, apex edge 222 is in contact with the portion of second inner surface 205. Likewise, apex edge 223 is in close proximity to the portion of first inner surface 204 that faces apex edge 223. In some embodiments, apex edge 223 is in contact with the portion of first inner surface 204. In some embodiments, as shown in FIG. 7B and FIG. 4A, apex edges 222 and 223 correspond to a longitudinal center line of the portion of the second or first inner surface 205, 204, respectively. In the embodiment shown in FIG. 7B, extruded gable feature 219 of protrusion 212 and extruded gable feature 220 of protrusion 213 meet (or mate with) the planar portions of first and second inner surfaces 204 and 205, respectively.

As shown in FIG. 7B, protrusions 212 and 213 are disposed side by side with each other, each facing a portion of the inner surfaces on the opposite leg member. A cavity 221 is formed by the protrusions 212 and 213, and the portions of first and second inner surfaces 204 and 205. Specifically, cavity 221 is formed by a slant side surface of gable structure 219 of protrusion 212, a slant side surface of gable structure 220 of protrusion 213, a portion of second inner surface 205 that is located between apex edges 222 and 223, and a portion of first inner surface 204 that is located between apex edges 222 and 223. It is understood that an array of occlusion cavities 221 are created at different locations in the longitudinal direction by the protrusions on the first and second leg members 201 and 202 when surgical clip 200 is in the closed position. The cavities 221 extend along the longitudinal direction of the leg members 201 and 202. FIG. 7B illustrates one of the occlusion cavities 221.

FIG. 7B also shows example dimensions of protrusions 212 and 213, portions of first and second inner surfaces 204 and 205 that faces the protrusions, and cavity 221 created by the protrusions and the portions of the inner surfaces. The dimensions are shown for illustrative purposes, and other dimensions are also possible. As shown in FIG. 7B, first inner surface 204 (or first leg member 201) may have the same width as second inner surface 205 (or second leg member 202). The width is designated as d5. The distance between apex edges 222 and 223 of protrusions 212 and 213 that are disposed side by side is designated as d2. The distance d2 may be between approximately (or about) (d5)/4 and approximately (or about) (d5)*(¾), or between about 25% of d5 and about 75% of d5. In some embodiments, distance d2 may be greater than or less than the above range. In FIG. 7B, apex edges 222 and 223 are shown to be substantially sharp, but in some embodiments they may be rounded or other shapes, or include additions such as roughness structures or treads.

A distance d3 is measured from apex edge 223 to the nearest side wall 224 of second leg member 202. Likewise, a distance d4 is measured from peak 222 to the nearest side wall 225 of first leg member 201. Distances d3 and d4 may each range from approximately (or about) 0 to approximately (or about) (⅜)*d5, and need not equal each other.

Two sides (left and right) of cavity 221 are formed by the inner side faces of gable structures 219 and 220. The other two sides (top and bottom) of cavity 221 are formed by portions of planar inner surfaces 204 and 205 that are located between apex edges 222 and 223. Angles α1 and α2 are measured from planar first inner surface 204 to the two slant side surfaces of gable structure 220, respectively. Angles α3 and α4 are measured from planar second inner surface 205 to the two slant side surfaces of gable structure 219, respectively. Angles α1, α2, α3, and α4 can range from approximately (or about) 5 degrees to approximately (or about) 85 degrees. In the embodiment shown in FIG. 7B, these four angles are equal. In other embodiments, any two of the angles α1, α2, α3, and α4 may not be equal.

As shown in FIG. 7B, cavity 221 may include a rhombal or parallelogrammatic cross section. When side surfaces of the gable structures 219 and 220 are curved, as shown in FIGS. 3G-3H, the shape of the cross section of cavity 221 may be a rhombus or parallelogram type shape with curved sides.

In some embodiments, a gap between the base of gable structure 219 (or gable structure 220) and planar second inner surface 205 (or planar first inner surface 204) is the same on both sides. The gap is designated by distance d1 in FIG. 7B. In other embodiments, the distance d1 may be different on both sides. In some embodiments, the distance d1 (i.e., gap between base of a gable structure and planar inner surface) may be greater than, less than, or equal to distance d2 (i.e., distance between apex edges 222 and 223).

The total cross sectional area of the gap between legs 201 and 202 in the closed position can be defined by (d1)*(d5) (omitting the protruding features). The cross sectional area Ac of cavity 221 created by gable structures 219 and 220 can be determined based on one or more distances d1-d8 shown in FIG. 7B. For example, the cross sectional area of cavity 221 may be defined as Ac=(d1*d5)−(d1)*(d3)−(d1*d4)−(d1*d7)/2−(d1*d8)/2, where distance d7 is the distance between apex edge 222 and the left bottom edge of gable structure 219 as shown in FIG. 7B, and distance d8 is the distance between apex edge 223 and the right bottom edge of table structure 220 as shown in FIG. 7B. In some embodiments, for example, when the cross section of cavity 221 is a rhombus or parallelogram, the cross sectional area of cavity 221 may be defined as Ac=d1*d6, where distance d6 a length of the top (or bottom) side of the parallelogram shape, or distance d6 is the distance between apex edge 222 and a bottom edge of an inner side surface of gable structure 220, as shown in FIG. 7B. The ratio between the cross sectional area Ac of cavity 221 and the total cross sectional area of the gap between legs 201 and 202 in the closed position may be defined as Ac/(d1*d5). The ratio Ac/(d1*d5) may range from approximately (or about) 0.2 to approximately (or about) 0.8.

FIG. 8A is a perspective view of surgical clip 200 in a closed position clamping a blood vessel 218, according to an embodiment of the present disclosure. First and second leg members 201 and 202 are engaged with each other and secured by the latch mechanisms 206 and 207. First and second leg members 201 and 202 traverse blood vessel 218 in a lateral direction of blood vessel 218. Accordingly, the protrusions provided on the inner surfaces of first and second leg members 201 and 202 traverse blood vessel 218 in the lateral direction of blood vessel 218. As described below, with the disclosed arrangement and geometric shape of the protrusions, surgical clip 200 can provide a suitable closure force while preventing sliding along the longitudinal direction of blood vessel 218. Although blood vessel 218 is shown in FIG. 8A, surgical clip 200 may also be used to ligate tissue structures.

FIG. 8B is a cross sectional view taken from the B-B' line of surgical clip 200 shown in FIG. 8A. As shown in FIG. 8B, upon closing of surgical clip 200, a portion of vessel or tissue 218 is forced along the sloping side surfaces of protrusions 212 and 213 into occlusion cavity 221. The portion of blood vessel 218 disposed within cavity 221 forms a "knot" that cannot exit from cavity 221 through the narrow channel formed between apex edge 222 and the portion of second inner surface 205 facing apex edge 222, and the narrow channel formed between apex edge 223 and the portion of first inner surface 204 facing apex edge 223.

Figure 9B:
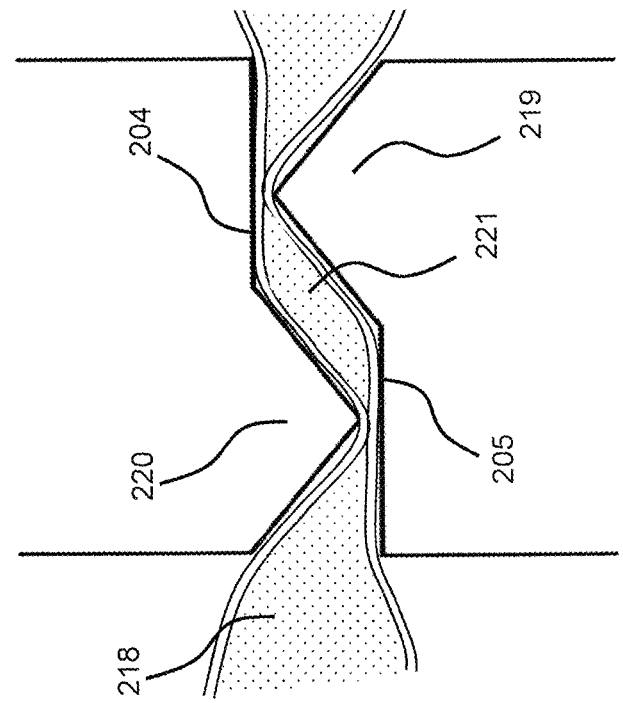
FIG. 9B is a cross sectional view of the surgical clip of FIG. 9A when first and second leg members are in the closed position, according to an embodiment of the present disclosure.
Figure 9A:
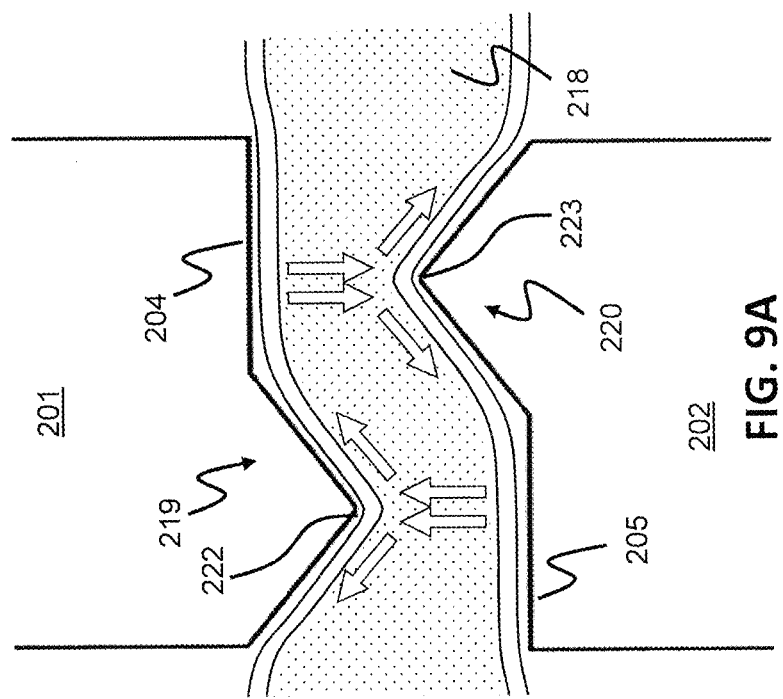
FIG. 9A is a cross sectional view of the surgical clip taken at the B-B' line shown in FIG. 8A before first and second leg members are closed, according to an embodiment of the present disclosure.

FIG. 9A is a cross-sectional view of surgical clip 200 taken at the B-B' line shown in FIG. 8A before first and second leg members 201 and 202 are closed, showing protrusions 212 and 213 at a position when first and second leg members 201 and 202 are approaching the closed position. FIG. 9B is a cross sectional view of surgical clip 200 when first and second leg members 201 and 202 are in the closed position. FIGS. 9A-9B illustrate how the protrusions with desirable geometric shapes can encourage the capture of the maximum amount of tissue and fluid in the occlusion cavity 221. The arrows in FIG. 9A illustrate the movement of a portion of blood vessel 218 (or a tissue structure) as surgical clip 200 is closing. FIGS. 9A-9B show that the apex edges 222 and 223 of gable structures 219 and 220 effectively push blood vessel 218 (or the tissue structure) and/or fluid contained therein into occlusion cavity 221.

Although planar surfaces are shown for first inner surface 204 and second inner surface 205, as well as side surfaces of gable structures 219 and 220, in some embodiments, one or more of these surfaces may include one or more roughness structures shown in FIG. 3I.

Figures 2A, 2B:
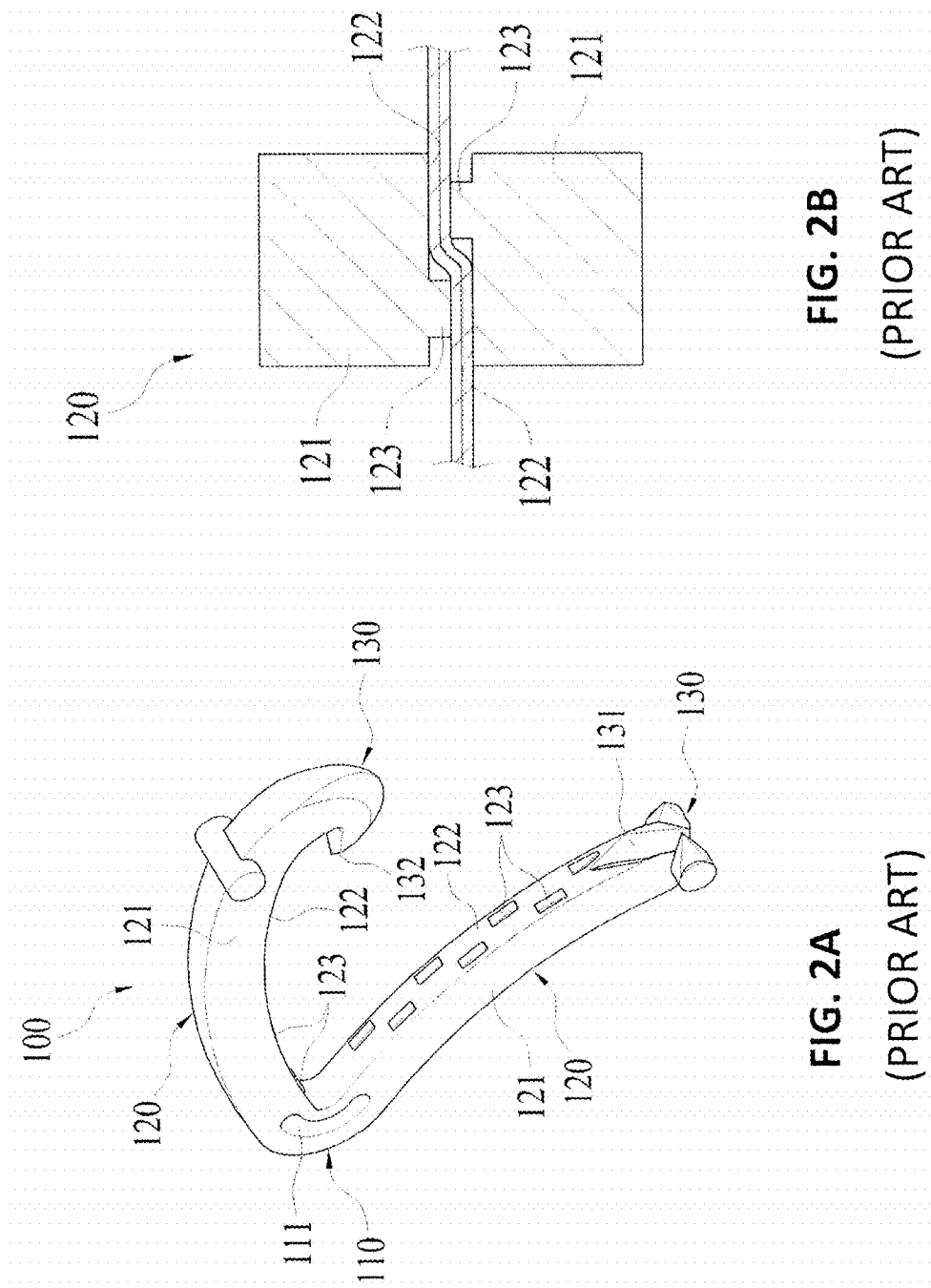
FIGS. 2A-2B show a surgical clip disclosed in the '454 publication.

Comparing the occlusion cavity 221 shown in FIGS. 8B and 9B, which is created by the slant side surfaces of protrusions 212 and 213, with the square/rectangle shaped cavity in FIG. 2C, created by straight vertical edges of the protrusions of the clip disclosed in the '454 publication, the slant side surfaces of the disclosed protrusions 212 and 213 allow and facilitate blood vessel 218 to deflect into occlusion cavity 221, thereby substantially fully occupy cavity 221, whereas the protrusions of the clip disclosed in the '454 publication do not facilitate the blood vessel to deflect into the cavity and fully occupy the cavity. With the disclosed surgical clip, the tissue and/or fluid retained/trapped in the occlusion cavity 221 impede migration of surgical clip 200 along the longitudinal direction of blood vessel 218. Moreover, both at the time of ligation and a certain amount of time (e.g., several days) following the surgery when the tissue becomes necrotic, the necrotic tissue within cavities 221 provides additional resistance against the physiological forces of blood flow, thereby further preventing surgical clip 200 from sliding along the longitudinal direction of blood vessel 218.

Furthermore, the geometric shapes of protrusions 212 and 213 can reduce the lateral force blood vessel 218 exerts on surgical clip 200. As shown in FIGS. 9A and 9B, each of protrusions 212 and 213 includes an apex edge (or peak) 222 and 223, respectively. Apex edges 222 and 223 minimize the area by which force is transferred from surgical clip 200 to blood vessel 218 (or other tissue structure). This minimum area maximizes the pressure that the gable structures of protrusions 212 and 213 apply to the clipped blood vessel 218 or tissue structures. The apex edges 222 and 223 of the gable structures are perpendicular to blood vessel 218 being ligated in the lateral direction of blood vessel 218, as shown in FIGS. 8A-9B. Therefore, the lines of maximized pressure on blood vessel 218 are also oriented perpendicular to (i.e., in the lateral direction of) blood vessel 218 being ligated. Maximizing the pressure the gable structures of protrusions 212 and 213 exert on blood vessel 218 in this orientation maximizes the impedance of migration of surgical clip 200 along the longitudinal direction of blood vessel 218 (e.g., the left-right direction in the cross-sectional view of FIG. 9A). Surgical clip 200 maximizes the pressure interface between surgical clip 200 and blood vessel 218 being ligated. Thus, the disclosed surgical clip increases the resistance, or anti-migration force applied through the increased pressure at the apex edges when locked in the closed position, thereby preventing migration in the longitudinal direction of the blood vessel or tissue structure.

The relationship between the migration force, migration resistance, and pressure can be described by the following equation, $$F_m = C_m * F_p$$

where $F_m$ is a migration force required to cause the surgical clip to slide off of the blood vessel or tissue structure that is clamped, $C_m$ is a coefficient of migration resistance, and $F_p$ is a pressure contacting the blood vessel or tissue structure. $F_p$ is defined as $$F_p = \frac{F_c}{A_e}$$

where $F_c$ is a force provided by the closed surgical clip, and $A_e$ is an area of an extruded surface. The area $A_e$ may be defined as an area of contact between a top portion of the protrusion and the portion of first or second inner surface that mates with the top portion. For example, the area $A_e$ can be defined as the area of contact between apex edge 222 and the portion of second inner surface 205 that mates with apex edge 222, or the area of contact between apex edge 223 and the portion of first inner surface 204. For a certain amount of force $F_c$, decreasing $A_e$ can drastically increase the pressure $F_p$, thereby increasing the migration force of the surgical clip. As shown in FIGS. 7B, 8B, and 9B, in surgical clip 200, by using the gable structures having apex edges 222 and 223, the area $A_e$ is drastically reduced, resulting in a drastic increase in the pressure $F_p$.

FIG. 10A illustrates a cross sectional view of surgical clip 200, according to another embodiment of the present disclosure. As shown in FIG. 10A, first inner surface 204 may include a recess 335 disposed at a location corresponding to apex edge 223 of gable structure 220, for receiving (or mating with) apex edge 223. Optionally, second inner surface 205 may also include a recess 340 disposed at a location corresponding to apex edge 222 of gable structure 219, for receiving (or mating with) apex edge 222. Recesses 335 and 340 may include shapes that match apex edges 223 and 222, respectively. For example, recesses 335 and 340 may include a cross section that is substantially triangular.

FIG. 10B illustrates a cross sectional view of surgical clip 200 shown in FIG. 10A in a closed position. In the closed position, cavity 221 is formed, as shown in FIG. 10B. Instead of pushing a portion of blood vessel 218 against a planar surface, a portion of blood vessel 218 is pushed into recess 340 by apex edge 222, and a portion of blood vessel 218 is pushed into recess 335 by apex edge 223. Recesses 335 and 340 may provide additional resistance to migration or sliding along the longitudinal direction of blood vessel 218.

FIGS. 11A-11B illustrate cross sectional views of surgical clip 200 in a position approaching a closed position, and in the closed position, respectively, according to an embodiment of the present disclosure. FIGS. 11A-11B are similar to FIGS. 9A-9B, except that roughness structures 330 are shown on at least one of inner surfaces 204 and 205, and side surfaces of gable structures 219 and 220. For example, as shown in FIGS. 11A-11B, all of the inner surfaces 204 and 205, and side surfaces of gable structures 219 and 220 are shown to include roughness structures 330. In some embodiments, only the inner side surfaces of gable structures 219 and 220 and the inner portions of the inner surfaces 204 and 205 that form cavity 221 include roughness structures 330, while the outer side surfaces of gable structures 219 and 220 and the outer portions of inner surfaces 204 and 205 do not include roughness structures. The roughness structures 330 disposed on the surfaces, including the surfaces that form cavity 221, provide additional resistance to migration of surgical clip 200 in the longitudinal direction of blood vessel 218. The roughness structures shown in FIG. 11A may also be included in recess 335, recess 340, or both shown in FIG. 10A.

FIGS. 12A-12E illustrate an additional structure and geometric shapes the protrusions can have, according to other embodiments of the present disclosure. The structure and shapes disclosed in FIGS. 12A-12E may replace the gable structure and shapes included in the embodiments shown in FIGS. 3A-11B. Instead of having a gable structure, at least one of protrusions disposed on first inner surface 204 and/or second inner surface 205 may have a structure that includes a longitudinally extended body with a base 405, a top surface 410, two side surfaces 406 and 407, and a cross section 415.

As shown in FIG. 12B, cross section 415 has a trapezoidal shape. Base 405 includes a first width w1 and top surface 410 includes a second width w2, which is smaller than first width w1. In some embodiments, second width w2 is about 5%-50% of first width w1. For example, second width w2 may be 5%, 10%, or 15% of first width w1. The top surface 410 may be configured to have a sufficiently narrow top surface (i.e., sufficiently small second width w2) to ensure a desirable pressure is achieved when surgical clip 200 clamps a blood vessel or tissue structure. As the second width w2 approaches zero, the trapezoidal cross section 415 approaches a triangle, and hence the structural shown in FIG. 12A approaches gable structure 300 shown in FIG. 3B.

Features that may be included in the gable structure 300, as discussed above, may also be included in structure 400. For example, FIG. 12C shows that structure 400 may include roughness structures 330 on at least one surface, for example, on top surface 410 (or a portion of top surface 410). In some embodiments, roughness structures 330 may also be included on both side surfaces 406 and 407 (or portions of side surfaces 406 and 407). In some embodiments, roughness structures 330 may be included on only one of side surfaces 406 and 407 (or a portion of the one of side surfaces 406 and 407).

FIG. 12D shows that top surface 410 may include a concave surface 410A. Although concave surface 410A is shown to span across the entire width w2 of top surface 410, in some embodiments, concave surface 410 may span only a portion of width w2 of top surface 410. Concave surface 410A may include a suitable radius of curvature. In some embodiments, more than one concave surface 410A may be provided on top surface 410, forming a wavy surface. Roughness structures 330 shown in FIG. 12C may be included on at least one surface of the embodiment of structure 400 shown in FIG. 12D, such as on at least one of concave surface 410A, the left side surface 406, or the right side surface 407.

FIG. 12E shows that top surface 410 may include a convex surface 410B. Although convex surface 410B is shown to span across the entire width w2 of top surface 410, in some embodiments, convex surface 410B may span only a portion of width w2 of top surface 410. Convex surface 410B may include a suitable radius of curvature. In some embodiments, more than one convex surface 410B may be provided on top surface 410. In some embodiments, top surface 410 may include a combination of concave surface 410A and convex surface 410B, forming a wavy surface. Roughness structures 330 shown in FIG. 12C may be included on at least one surface of the embodiment of structure 400 shown in FIG. 12E, such as on at least one of concave surface 410B, the left side surface 406, or the right side surface 407.

Protrusion 400 having the trapezoidal cross section may include other shapes that are variations of the shapes shown in FIGS. 12B-12E. For example, although an isosceles trapezoid is shown in FIG. 12B, the trapezoid may be other types, such as an acute trapezoid, a right trapezoid, an obtuse trapezoid, a 3-sided equal trapezoid, etc.

Protrusions 400 shown in FIGS. 12A-12E may be disposed on one leg member, or on both leg members of surgical clip 200. In some embodiments, protrusions 400 included on both leg members in surgical clip 200 may have the same shape and/or dimension. In some embodiments, protrusions 400 included on first leg member 201 may have a different shape and/or dimension from protrusions 400 included on second leg member 202. In some embodiments, protrusions 400 included on the same leg member (e.g., first or second leg member 201 or 202) may include the same shape and/or dimension. In some embodiments, protrusions 400 included on the same leg member may include different shape and/or dimension. For example, protrusions of different dimensions and/or shapes may be disposed on an inner surface of the same leg member. Above discussions about the different combination of shape and/or dimension for the protrusions in the embodiments disclosed in FIGS. 3A-11B are also applicable to the embodiments shown in FIGS. 12A-12E, and other embodiments shown in latter figures. Hence, such discussions are not repeated.

Figure 13B:
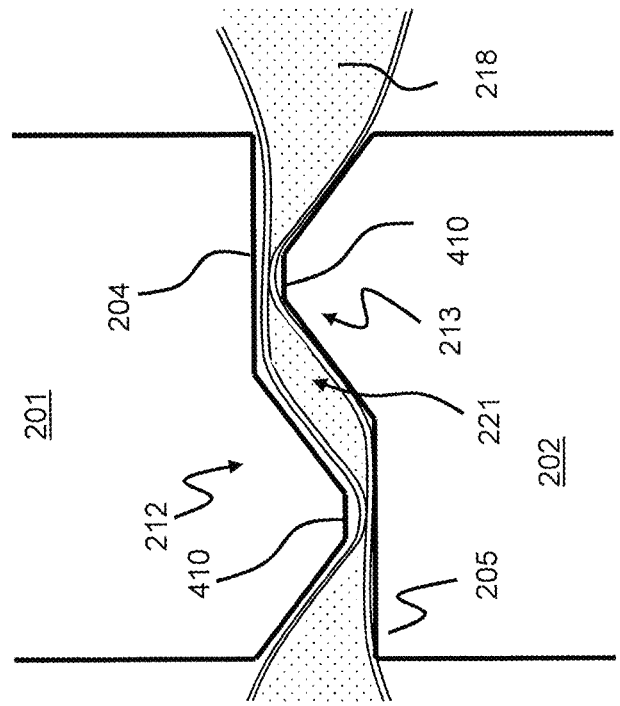
FIGS. 13A-13B illustrate cross sectional views of a surgical clip in a position approaching a closed position and in the closed position, respectively, according to an embodiment of the present disclosure.
Figure 13A:
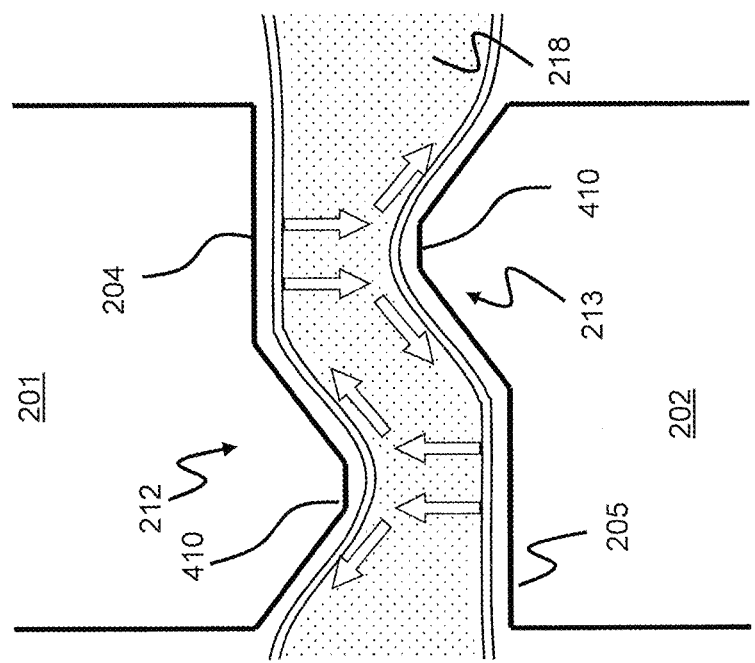

FIGS. 13A-13B illustrate cross sectional views of surgical clip 200 having protrusions in a position approaching a closed position and in a closed position, respectively. FIGS. 13A and 13B are similar to FIGS. 9A and 9B, except that apex edges 222 and 223 are replaced with top surfaces 410. Top surfaces 410 are configured to be sufficient narrow such that a sufficient pressure is created at the contact surface with blood vessel 218 when surgical clip 200 is in the closed position.

As shown in FIG. 13B, cavity 221 is created when surgical clip 200 is in the closed position. Cavity 221 is formed by two inner side surfaces of protrusions 212 and 213 that include structures 400, and portions of first and second inner surfaces 204 and 205 that are located between top surfaces 410 in the lateral direction of inner surfaces 204 and 205. As shown in FIG. 13A, a portion of blood vessel 218 is pushed into cavity 221 to substantially fill cavity 221. The portion of blood vessel 218 disposed within cavity 221 cannot exit the narrow channels formed by the inner surfaces 204, 205 and the corresponding top surfaces 410 of the protrusions when surgical clip 200 is in the closed position, thereby preventing migration or sliding along the longitudinal direction of blood vessel 218.

FIGS. 14A-14B illustrate cross sectional views of surgical clip 200 having protrusions in a position approaching a closed position and in the closed position, respectively. FIGS. 14A and 14B are similar to FIGS. 10A and 10B, except that apex edges 222 and 223 are replaced with top surfaces 410, respectively, and recesses 340 and 335 are replaced with recesses 440 and 435, respectively. Recesses 435 and 440 may include shapes that match top surfaces 410, respectively. For example, recesses 435 and 440 include a trapezoidal shape (including a flat horizontal surface and slant side surfaces) that matches a top portion (including top surface 410) of the trapezoidal shape of protrusions 212 and 213. Recesses 435 and 440 may receive (or mate with) a corresponding top surface 410. As shown in FIG. 14B, recesses 435 and 440 each receive a portion of blood vessel 218 that is clamped by protrusions 213 and 212 and the corresponding recesses 435 and 440 in the closed position.

Figure 15B:
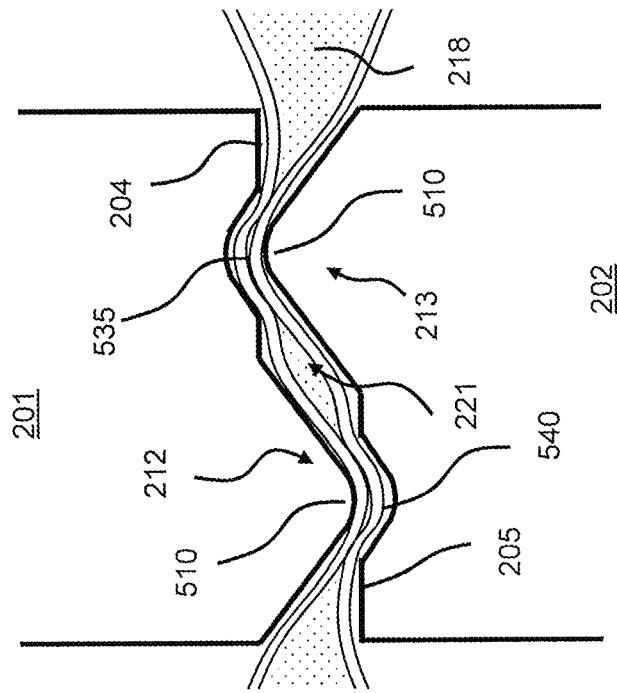
FIGS. 15A-15B illustrate cross sectional views of a surgical clip in a position approaching a closed position and in the closed position, respectively, according to another embodiment of the present disclosure.
Figure 15A:
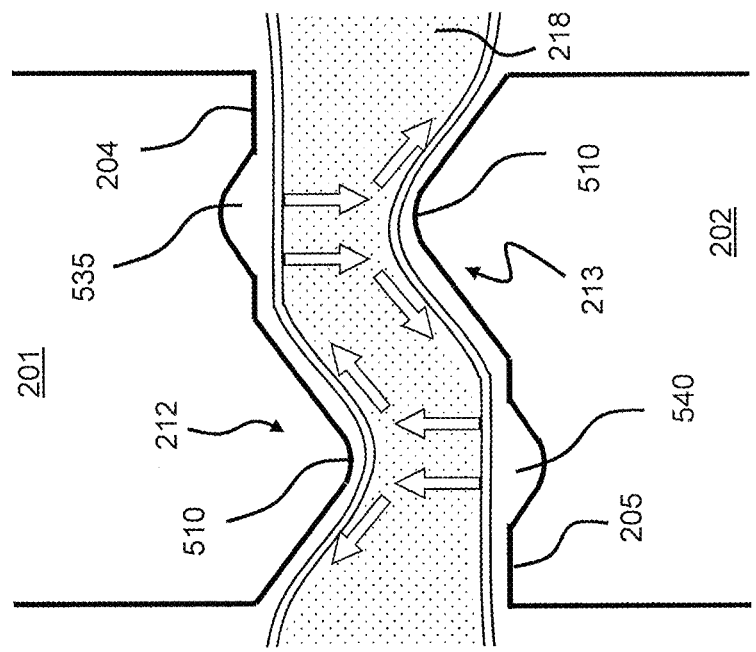

FIGS. 15A-15B illustrate surgical clip 200 having protrusions in a position approaching a closed position and in the closed position, respectively. FIGS. 15A and 15B are similar to FIGS. 14A and 14B, except that a curved top surface 510 replaces flat top surface 410, and curved recesses 540 and 535 replaces recesses 440 and 435 that have flat surfaces. Curved top surfaces 510 may include a convex surface, as shown in FIG. 15A, although other curved surfaces may also be included in top surface 510, such as one or more concave surfaces, or a mixture of concave and convex surfaces (e.g., a wavy surface).

Recess 540 includes a curved surface that matches curved top surface 510. A top portion of protrusion 212, including curved top surface 510, is received within recess 540. Thus, recess 540 matches or mates with the curved top portion (including curved top surface 510) of protrusion 212. Likewise, recess 535 includes a curved surface that matches curved top surface 510 of protrusion 213. Curved surface 535 may have a shape that is similar to that of curved surface 540. A top portion of protrusion 213, including top surface 510, is received within recess 535. As shown in FIG. 15B, in the closed position, curve top surface 510 pushes a portion of blood vessel 218 into recess 540 and recess 535.

Figure 16:
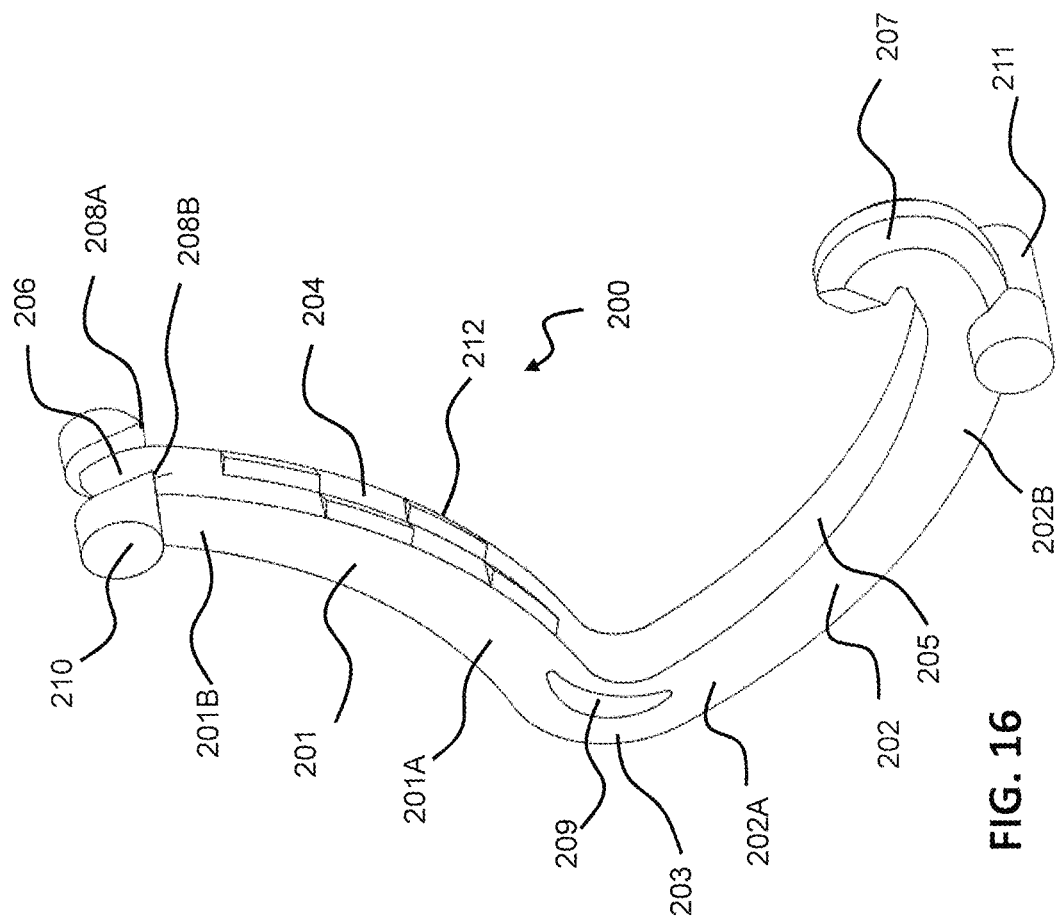
FIG. 16 shows a perspective view of a surgical clip according to another embodiment of the present disclosure.

FIG. 16 shows a perspective view of surgical clip 200 according to another embodiment of the present disclosure. As shown in FIG. 16, only one leg member is provided with protrusions. The other leg member has no complementary or matching protrusions. FIG. 16 is similar to FIG. 3A, except that only first leg member 201 are provided with a plurality of (e.g., two rows of) protrusions 212 on first inner surface 204, and second leg member 202 has no protrusions on second inner surface 205. It is possible that only second leg member 202 is provided with protrusions while first leg member 201 does not include protrusions. Although the embodiment shown in FIG. 16 is based on the embodiment shown in FIG. 3A to illustrate one example of a surgical clip having protrusions on only one leg member, other embodiments of surgical clip 200 disclosed herein may also be modified to have only one leg member being provided with a plurality of protrusions. Features included in other embodiments, such as those shown in FIGS. 3A-15B, may also be included in the embodiment shown in FIG. 16. The descriptions of such features are not repeated.

Other embodiments of surgical clip 200 are shown in FIGS. 17A-26C. FIGS. 17A-17C show a perspective view, a top view of an inner surface, and a cross sectional view of a surgical clip 200 according to another embodiment of the present disclosure. FIG. 17A is a perspective view of surgical clip 200 having a plurality of protrusions 612 and 613 disposed on first leg member 201 and second leg member 202, respectively. The embodiment shown in FIG. 17A includes features similar to those included in the embodiment shown in FIG. 3A, except that the protrusions are different as compared to those shown in FIG. 3A. In the embodiment shown in FIG. 17A, protrusions 612 and 613 each include an array of pyramid shaped protrusions. The bubble in FIG. 17A shows an enlarged view of a portion of second leg member 202 to better show the pyramid shape and the arrangement of the array of pyramid shaped protrusions. For example, each protrusion 612 or 613 may include six pyramid shaped protrusions, although other numbers (e.g., 1, 2, 3, 4, 5, 7, 8, 9, 10, etc.) of pyramid shaped protrusions may also be included in each protrusion 612 or 613.

Protrusions 612 are disposed in two rows in an alternating pattern including one or more protrusions 612 and one or more portions of first inner surface 204. Protrusions 612 extend in the longitudinal direction of first inner surface 204. Likewise, protrusions 613 are disposed on second inner surface 205 in two rows that complement the two rows disposed on first inner surface 204. Protrusions 613 are disposed in an alternating pattern in each row, including one or more protrusions 613 and one or more portions of second inner surface 205. Other features discussed above in connection with other embodiments may also be included in the embodiment shown in FIG. 17A, such as the roughness structures discussed above. The detailed descriptions of the similar features are not repeated.

FIG. 17B is a top view of inner surface 204 of first leg member 201 shown in FIG. 17A. It is understood that the top view of second inner surface 205 of second leg member 202 has an arrangement complementary to the top view shown in FIG. 17B. As shown in FIG. 17B, each protrusion 612 includes a length Lm and a width Ln. An aspect ratio defined by Lm/Ln is greater than or equal to 1.0. In other words, the length is greater than or equal to the width. For example, the aspect ratio Lm/Ln may be greater than 5.0, greater than 10.0, greater than 30.0, greater than 50.0, greater than 100.0, or greater than any other suitable number.

FIG. 17C is a cross sectional view of surgical clip 200 when both leg members 201 and 202 are brought close to each other. The cross sectional view shown in FIG. 17C may be taken along a lateral direction of the leg members when they are brought close to each other. As shown in FIG. 17C, each protrusion (e.g., 612 or 613) faces a portion of the inner surface (e.g., 205 or 204) on the opposite leg member. Features included in other embodiments, such as those shown in FIGS. 3A-16 may also be included in the embodiment shown in FIGS. 17A-17C. The descriptions of such features are not repeated.

Figures 18A, 18B, 18C:
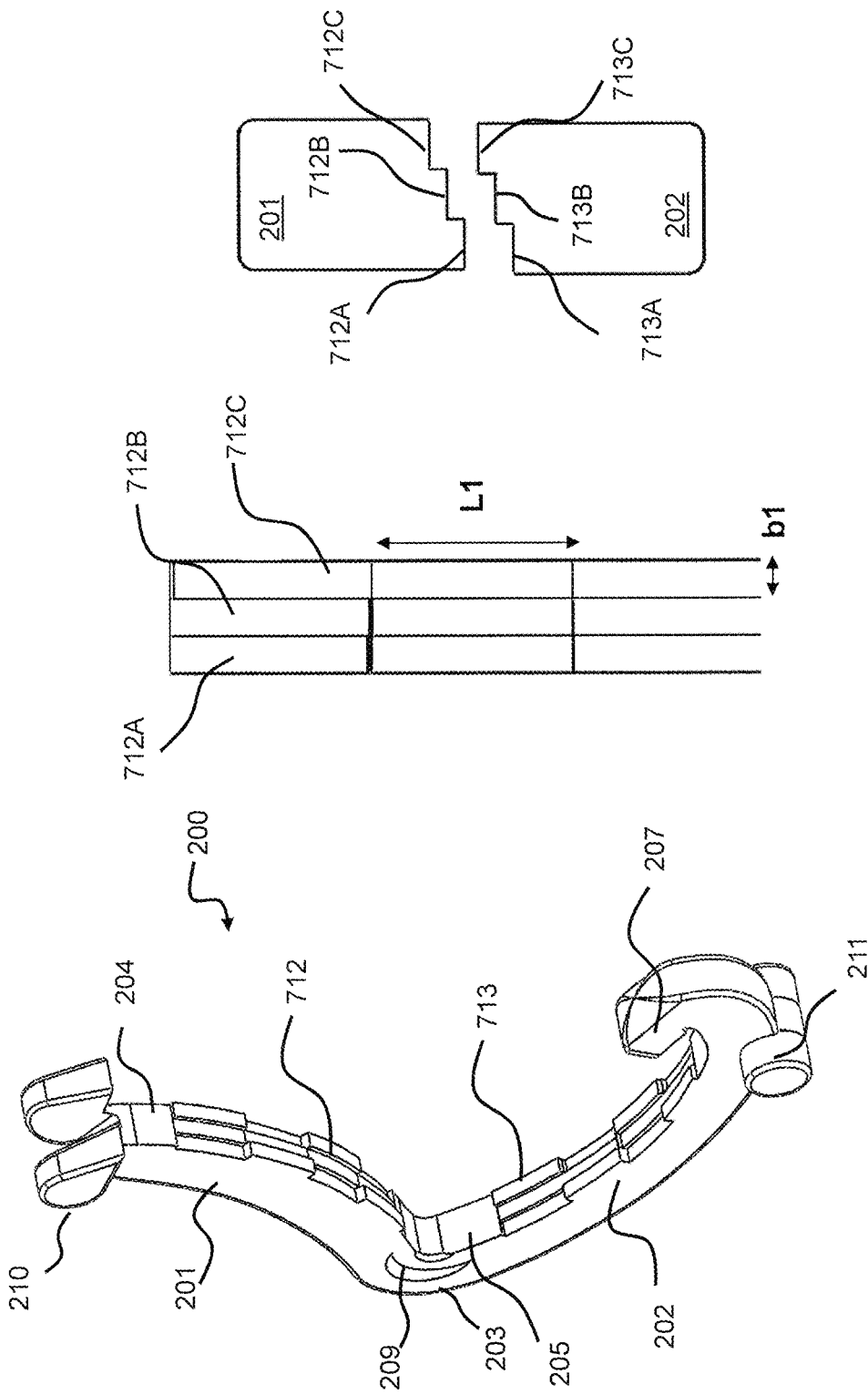
FIGS. 18A-18C show a perspective view, a top view of an inner surface, and a cross sectional view of a surgical clip according to another embodiment of the present disclosure.

FIGS. 18A-18C show a perspective view, a top view of an inner surface, and a cross sectional view of another embodiment of surgical clip 200. FIG. 18A shows a perspective view of surgical clip 200 having a first plurality of protrusion 712 on first inner surface 204, and a second plurality of protrusions 713 on second inner surface 205. FIG. 18A is similar to FIG. 3A, except that the protrusions have different shapes. Features included in other embodiments, such as those shown in FIGS. 3A-17C may also be included in the embodiment shown in FIGS. 18A-18C. The descriptions of such features are not repeated.

FIG. 18B is a top view of first or second inner surface 204 or 205. FIG. 18C shows a cross sectional view of surgical clip 200 when first and second leg members 201 and 202 are brought close to each other. Each protrusion 712 (or 713) has a three-step structure. Each protrusion 712 includes three protruded parts 712A, 712B, and 712C having different heights as measured from first inner surface 204. In some embodiments, one of protruded parts 712A, 712B, and 712C may be part of first inner surface 204 (hence the three-step structure may become a two-step structure). Additional row or rows of protruded parts having different heights may be added to the three-step structure to form a four-step structure, five-step structure, or a structure with any suitable number of steps. Each protrusion 712 includes a length L1 and a width b1. Length L1 is greater than or equal to width b1. The ratio between L1 and d1 is greater than or equal to 1.0, such as greater than 2.0, greater than 5.0, greater than 10.0, greater than 30.0, greater than 50.0, greater than 100.0, or greater than any other suitable number.

As shown in FIGS. 18A and 18C, second leg member 202 includes a plurality of protrusions 713 that complement protrusions 712 provided on first leg member 201. For example, each protrusion 713 may include a three-step structure including three protruded parts 713A, 713B, and 713C with different heights as measured from second inner surface 205. In some embodiments, one of the protruded parts 713A, 713B, and 713C may be part of second inner surface 205 (hence, the three-step structure becomes a two-step structure). Additional row or rows of protruded parts having different heights may be added to the three-step structure to form a four-step structure, five-step structure, or a structure with any suitable number of steps. Protruded parts in each row in the longitudinal direction (on first inner surface 204 or second inner surface 205) include the same height. Other features included in other embodiments shown in FIGS. 3A-17C discussed above may also be included in the embodiment shown in FIGS. 18A-18C. Descriptions of such features are not repeated.

Figure 19B:
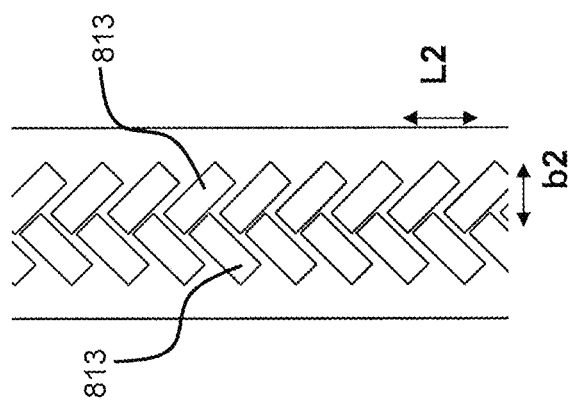
FIGS. 19A-19B show a perspective view and a top view of an inner surface of a surgical clip according to another embodiment of the present disclosure.
Figure 19A:
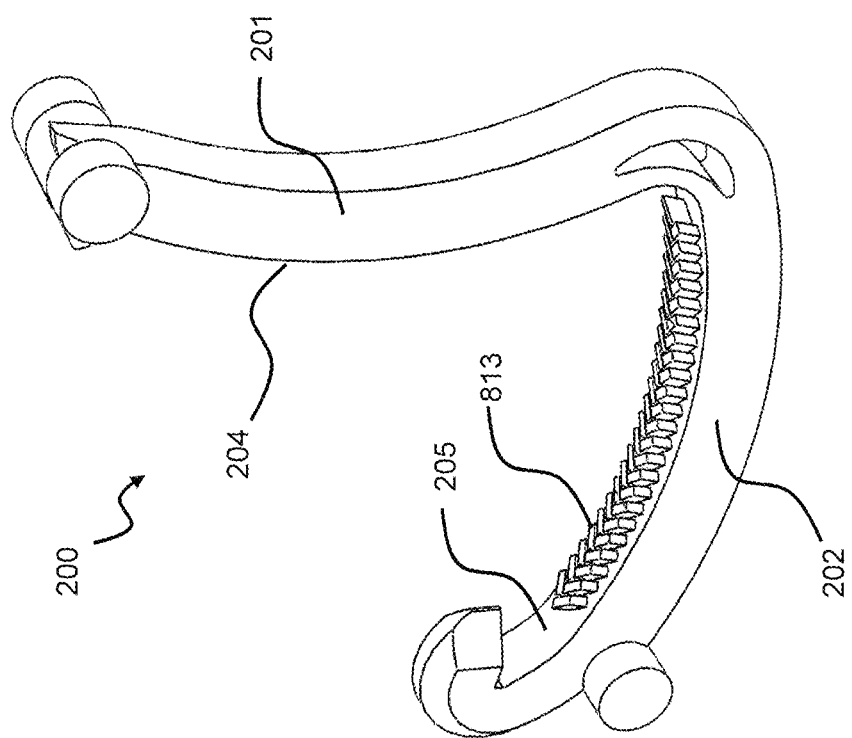

FIGS. 19A-19B show a perspective view and a top view of an inner surface of another embodiment of surgical clip 200. FIG. 19A is a perspective view of surgical clip 200. Surgical clip 200 shown in FIG. 19A may include features similar to those shown in FIG. 3A and other figures, such as any of FIGS. 3B-18C, except that the protrusions provided on at least one of the inner surfaces of the two leg members have a different shape. FIG. 19A shows that second inner surface 205 is provided with a plurality of protrusions 813. In some embodiments, only first inner surface 204 may be provided with protrusions. First inner surface 204 may or may not be provided with complementary protrusions. Protrusions 813 may cover a suitable closure area in a closed position, such as 60%-90% of the surface area of second inner surface 205.

FIG. 19B shows a top view of second inner surface 205 shown in FIG. 19A. It is understood that when first inner surface 204 is also provided with complementary protrusions, the top view of first inner surface 204 may be similar to or complementary to the top view shown in FIG. 19B. The top view shows the arrangement and dimension of protrusions 813. Protrusions 813 may be arranged in a bricklayer pattern. Protrusions 813 may be arranged in two rows. Two adjacent protrusions 813 laterally disposed side by side may form a certain angle, such as 90 degrees, 100 degrees, 80 degrees, or any other suitable degrees. The two adjacent protrusions are repeated longitudinally along second inner surface 205 to form the bricklayer pattern. The length of each protrusion 813 projected in the longitudinal direction of second inner surface 205 is designated as L2, and the length projected in the lateral direction is designated as b2. The ratio between L2 and b2 is greater than or equal to 1.0, such as 1.5, 2.0, 2.5, 3.0, 3.5, 4.0, or any other suitable number. Other features included in other embodiments shown in FIGS. 3A-18B discussed above may also be included in the embodiment shown in FIGS. 19A-19B. Detailed descriptions of such features are not repeated.

FIGS. 20A-20B show a perspective view and a top view of an inner surface of another embodiment of surgical clip 200. FIG. 20A is a perspective view of surgical clip 200. Surgical clip 200 shown in FIG. 20A may include features similar to those shown in FIG. 3A and other figures, such as any of FIGS. 3B-19B, except that the protrusions provided on at least one of the inner surfaces of the two leg members have a different shape. FIG. 20A shows that second inner surface 205 is provided with a plurality of protrusions 913. First inner surface 204 may or may not be provided with complementary protrusions. In some embodiments, only first inner surface 204 may be provided with protrusions. Protrusions 913 may cover a suitable closure area in a closed position, such as 60%-90% of the surface area of second inner surface 205.

FIG. 20B is a top view of second inner surface 205. It is understood that when first inner surface 204 is also provided with complementary protrusions, the top view of first inner surface 204 may be similar to or complementary to the top view shown in FIG. 20B. The top view shows the arrangement and dimension of protrusions 913. Protrusions 913 form a tire pattern. Each protrusion 913 includes two pieces integrally jointed together at a certain angle. The protrusions 913 may be arranged in one row, two rows, three rows, or any other suitable number of rows. The length of each protrusion 913 in the longitudinal direction of second inner surface 205 is designated as L3, and the width in the lateral direction is designated as b3. The ratio between L3 and b3 is greater than or equal to 1.0, such as 1.5, 2.0, 2.5, 3.0, 3.5, 4.0, or any other suitable number. Other features included in other embodiments shown in FIGS. 3A-19B discussed above may also be included in the embodiment shown in FIGS. 20A-20B. Detailed descriptions of such features are not repeated.

Figure 21B:
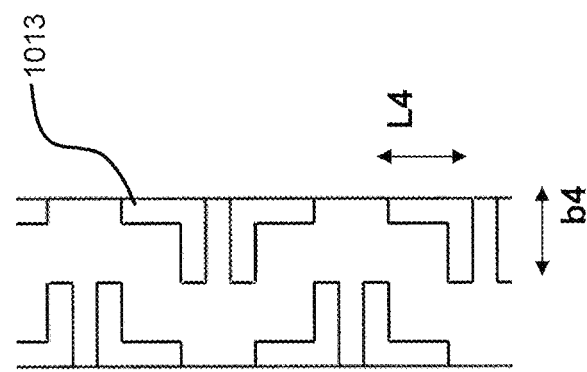
FIGS. 21A-21B show a perspective view and a top view of an inner surface of a surgical clip according to another embodiment of the present disclosure.
Figure 21A:
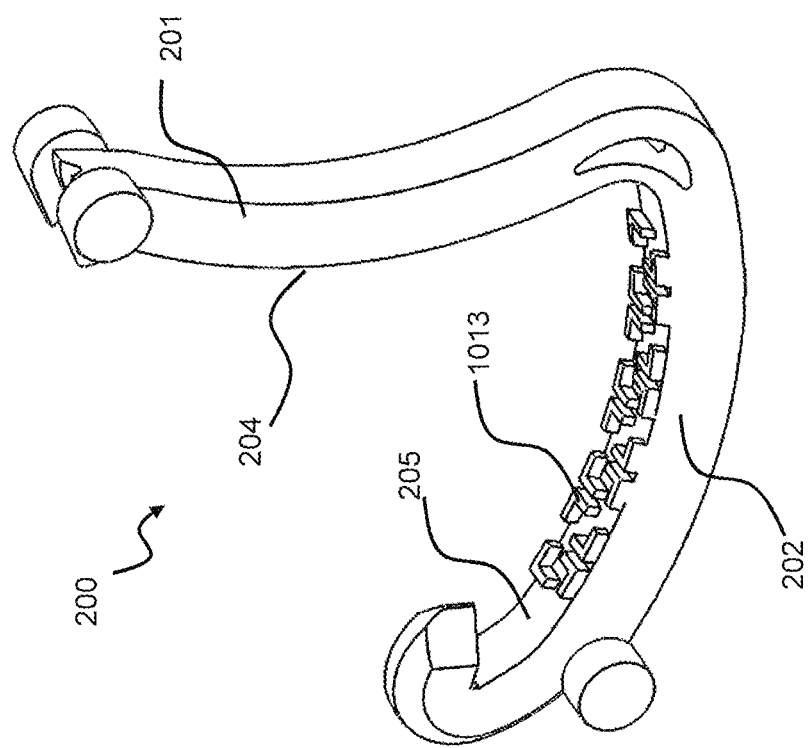

FIGS. 21A-21B show a perspective view and a top view of an inner surface of another embodiment of surgical clip 200. FIG. 21A is a perspective view of surgical clip 200. Surgical clip 200 shown in FIG. 21A may include features similar to those shown in FIG. 3A and other figures, such as any of FIGS. 3B-20B, except that the protrusions provided on at least one of the inner surfaces of the two leg members have a different shape. FIG. 21A shows that second inner surface 205 is provided with a plurality of protrusions 1013. First inner surface 204 may or may not be provided with complementary protrusions. In some embodiments, only first inner surface 204 may be provided with protrusions. Protrusions 1013 may cover a suitable closure area in a closed position, such as 60%-90% of the surface area of second inner surface 205.

FIG. 21B is a top view of second inner surface 205. It is understood that when first inner surface 204 is also provided with complementary protrusions, the top view of first inner surface 204 may be similar to or complementary to the top view shown in FIG. 21B. The top view shows the arrangement and dimension of protrusions 1013. Protrusions 1013 may include an L-shape (in the top view) and may be oriented in different manners on second inner surface 205. For example, some protrusions 1013 are rotated 180 degrees as compared to others. A length of each protrusion 1013 in the longitudinal direction of second inner surface 205 is designated as L4, and a length in the lateral direction is designated as b4. The ratio between L4 and b4 is greater than or equal to 1.0, such as 1.5, 2.0, 2.5, 3.0, 3.5, 4.0, or any other suitable number. Other features included in other embodiments shown in FIGS. 3A-20B discussed above may also be included in the embodiment shown in FIGS. 21A-21B. Detailed descriptions of such features are not repeated.

Figure 22B:
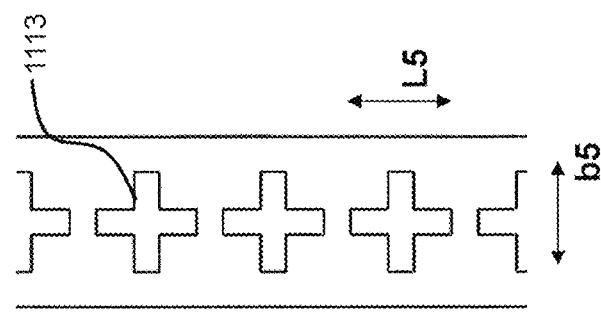
FIGS. 22A-22B show a perspective view and a top view of an inner surface of a surgical clip according to another embodiment of the present disclosure.
Figure 22A:
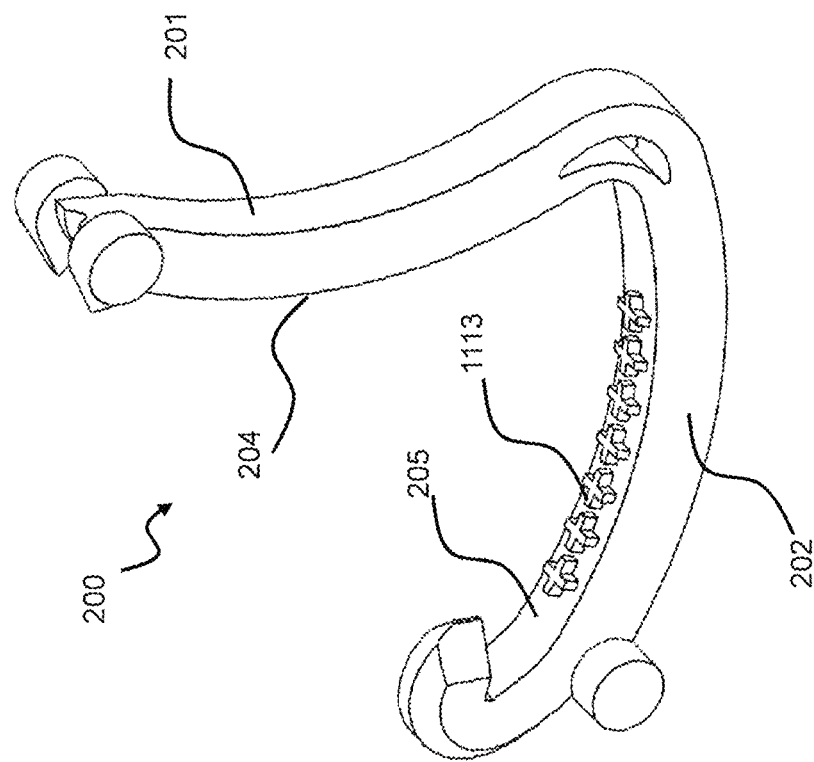

FIGS. 22A-22B show a perspective view and a top view of an inner surface of another embodiment of surgical clip 200. FIG. 22A is a perspective view of surgical clip 200. Surgical clip 200 shown in FIG. 22A may include features similar to those shown in FIG. 3A and other figures, except that the protrusions provided on at least one of the inner surfaces of the two leg members have a different shape. FIG. 22A shows that second inner surface 205 is provided with a plurality of protrusions 1113. First inner surface 204 may or may not be provided with complementary protrusions. In some embodiments, only first inner surface 204 may be provided with protrusions. Protrusions 1113 may cover a suitable closure area in a closed position, such as 60%-90% of the surface area of second inner surface 205.

FIG. 22B is a top view of second inner surface 205. It is understood that when first inner surface 204 is also provided with complementary protrusions, the top view of first inner surface 204 may be similar to or complementary to the top view shown in FIG. 22B. The top view shows the arrangement and dimension of protrusions 1113. Protrusions 1113 may include a cross shape in the top view and may be arranged in one or more rows. A length of each protrusion 1113 in the longitudinal direction of second inner surface 205 is designated as L5, and a width in the lateral direction is designated as b5. The ratio between L5 and b5 is greater than or equal to 1.0, such as 1.5, 2.0, 2.5, 3.0, 3.5, 4.0, or any other suitable number. Other features included in other embodiments shown in FIGS. 3A-21B discussed above may also be included in the embodiment shown in FIGS. 22A-22B. Detailed descriptions of such features are not repeated.

Figure 23B:
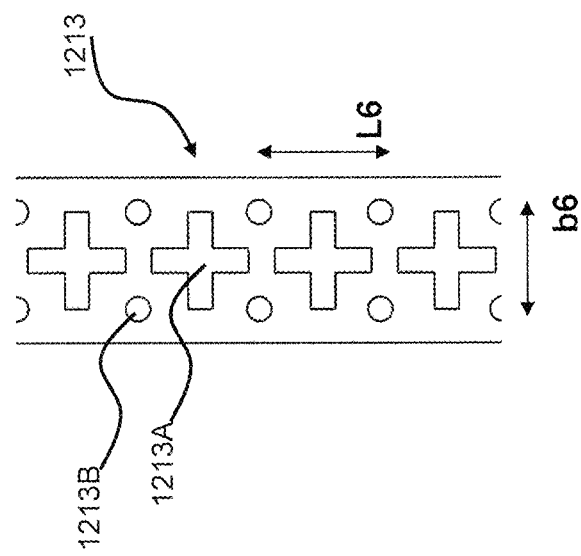
FIGS. 23A-23B show a perspective view and a top view of an inner surface of a surgical clip according to another embodiment of the present disclosure.
Figure 23A:
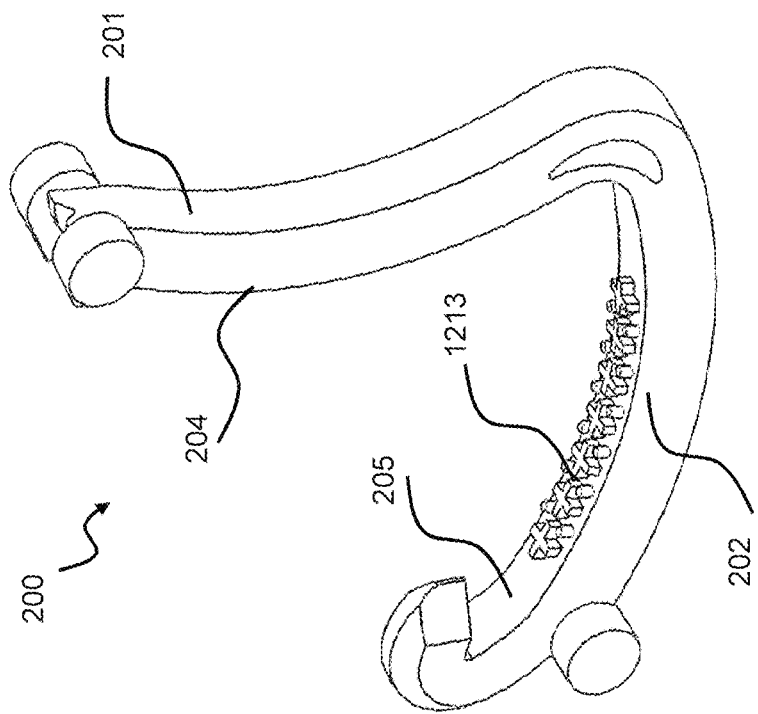

FIGS. 23A-23B show a perspective view and a top view of an inner surface of another embodiment of surgical clip 200. FIG. 23A is a perspective view of surgical clip 200. Surgical clip 200 shown in FIG. 23A may include features similar to those shown in FIG. 3A and other figures, except that the protrusions provided on at least one of the inner surfaces of the two leg members have a different shape. FIG. 23A shows that second inner surface 205 is provided with a plurality of protrusions 1213. First inner surface 204 may or may not be provided with complementary protrusions. In some embodiments, only first inner surface 204 may be provided with protrusions. Protrusions 1213 may cover a suitable closure area in a closed position, such as 60%-90% of the surface area of second inner surface 205.

FIG. 23B is a top view of second inner surface 205. It is understood that when first inner surface 204 is also provided with complementary protrusions, the top view of first inner surface 204 may be similar to or complementary to the top view shown in FIG. 22B. The top view shows the arrangement and dimension of protrusions 1213. Protrusions 1213 may include a cross protrusion 1213A having a cross shape in the top view and one or more round protrusions 1213B (e.g., a ball, a cylindrical structure, etc.) having a circle shape in the top view. Four round protrusions 1213B are shown surrounding each cross shape 1213A, although more or fewer round protrusions 1213B may be included in the pattern. Protrusions 1213 are shown to be arranged in one row, although they may be arranged in two or more rows. A length of each protrusion 1213 in the longitudinal direction of second inner surface 205 is designated as L6, and a width in the lateral direction is designated as b6. The ratio between L6 and b6 is greater than or equal to 1.0, such as 1.5, 2.0, 2.5, 3.0, 3.5, 4.0, or any other suitable number. Other features included in other embodiments shown in FIGS. 3A-22B discussed above may also be included in the embodiment shown in FIGS. 23A-23B. Detailed descriptions of such features are not repeated.

Figure 24C:
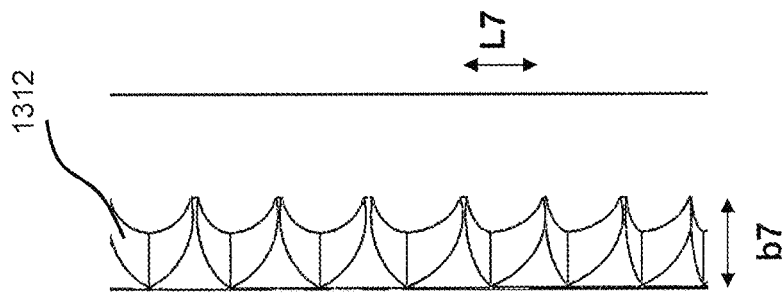
FIGS. 24A-24C show a perspective view, a cross sectional view, and a top view of an inner surface of a surgical clip according to another embodiment of the present disclosure.
Figure 24B:
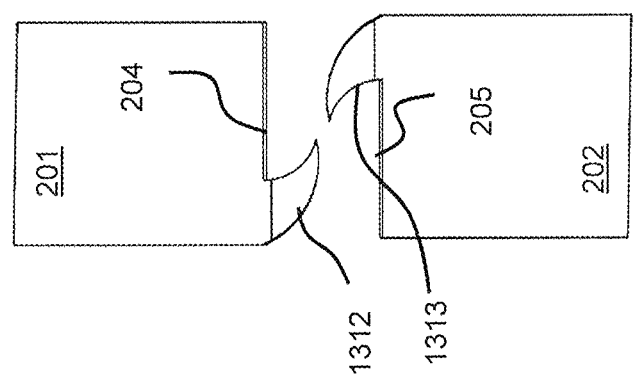
Figure 24A:
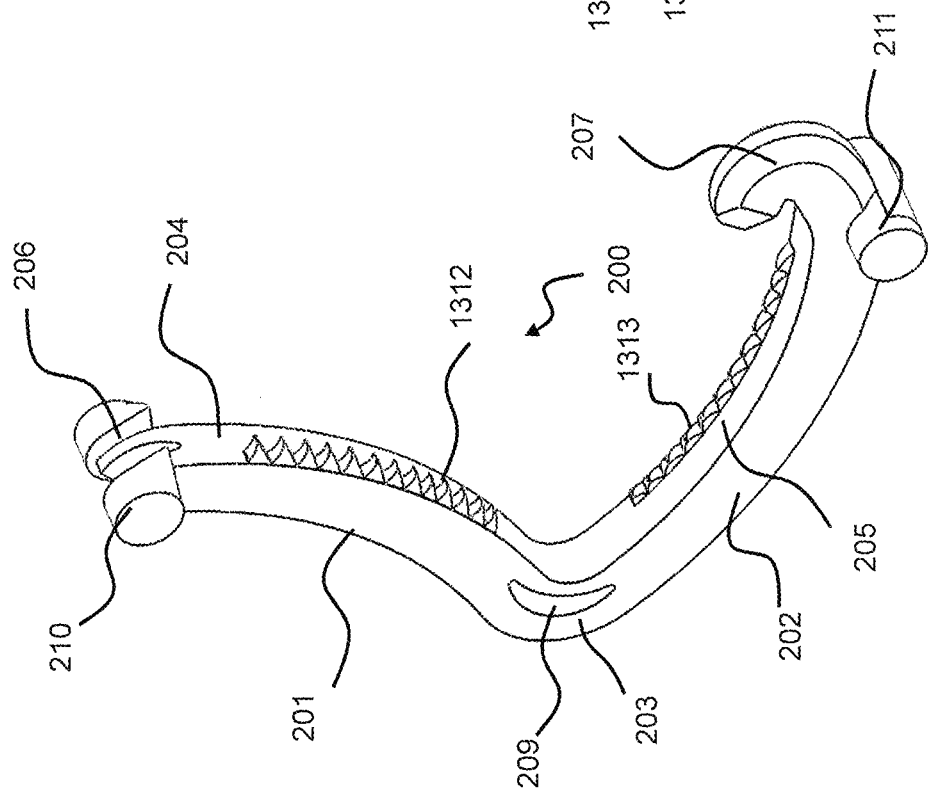

FIGS. 24A-24C show a perspective view, a cross sectional view, and a top view of an inner surface of another embodiment of surgical clip 200. FIG. 24A is a perspective view of surgical clip 200. Surgical clip 200 shown in FIG. 24A may include features similar to those shown in FIG. 3A and other figures, such as any of FIGS. 3B-23B, except that the protrusions provided on at least one of the inner surfaces of the two leg members have a different shape. FIG. 24A shows that first inner surface 204 is provided with a first plurality of protrusions 1312, and second inner surface 205 is provided with a second plurality of protrusions 1313. Protrusions 1312 and 1313 together may cover a suitable combined closure area in a closed position, such as 60%-90% of the surface area of first or second inner surface 204 or 205. Protrusions 1312 and 1313 may include a barb protruded feature.

FIG. 24B is a cross sectional view of surgical clip 200 when first and second leg members 201 and 202 are brought closer to each other. FIGS. 24A-24B show that protrusions 1312 having the barb protruded feature are disposed on one side of first inner surface 204 in the longitudinal direction, and protrusions 1313 having the bar protruded feature are disposed on another side (an opposite side) of second inner surface 205. Each protrusion 1312 or 1313 faces a portion of first or second inner surface 204 or 205. Each barb protruded feature includes a pointing tip portion.

In the closed position, two adjacent barb protruded features disposed side by side with each other may form a cavity (not shown in FIG. 24B), which may have an elliptical shape in the cross sectional view. In addition, in the closed position, the barb protruded features may penetrate into the blood vessel or tissue structure. This provides a transfixion of the blood vessel or tissue structure, thereby further increasing resistance to the migration or sliding along the longitudinal direction of the blood vessel or tissue structure.

Although one row of protrusions 1312 and one row of protrusions 1313 are shown on first and second leg members 201 and 202, respectively, additional row or rows of protrusions 1312 may be added to first leg member 201, and additional row or rows of protrusions 1313 may be added to second leg member 202.

FIG. 24C is a top view of first inner surface 204. It is understood that the top view of second inner surface 205 may be similar to or complementary to the top view shown in FIG. 24C. The top view shows the arrangement and dimension of protrusions 1312. Protrusions 1312 are shown to be arranged in one row, although they may be arranged in two or more rows. A length of each protrusion 1312 in the longitudinal direction of first inner surface 204 is designated as L7, and a width in the lateral direction is designated as b7. The ratio between L7 and b7 is greater than or equal to 1.0, such as 1.5, 2.0, 2.5, 3.0, 3.5, 4.0, or any other suitable number. Likewise, each protrusion 1313 may also include a ratio between its length and its width that is greater than or equal to 1. Other features included in other embodiments shown in FIGS. 3A-23B discussed above may also be included in the embodiment shown in FIGS. 24A-24C. Detailed descriptions of such features are not repeated.

FIGS. 25A-25C show a perspective view, a cross sectional view, and a top view of an inner surface of another embodiment of surgical clip 200. FIG. 25A is a perspective view of surgical clip 200. Surgical clip 200 shown in FIG. 25A may include features similar to those shown in FIG. 3A and other figures, such as any of FIGS. 3B-24C, except that the protrusions provided on at least one of the inner surfaces of the two leg members have a different shape. FIG. 25A shows that first inner surface 204 is provided with a protrusion 1412, and second inner surface 205 is provided with a plurality of protrusions 1413. Protrusion 1412 may be a single piece extended in the longitudinal direction of first inner surface 204. Protrusions 1412 and 1413 together may cover a suitable combined closure area in a closed position, such as 60%-90% of the surface area of first or second inner surface 204 or 205.

FIG. 25B is a cross sectional view of surgical clip 200 when first and second leg members 201 and 202 are brought closer to each other. FIGS. 25A-25B show that protrusions 1413 have the barb protruded features and are disposed at two sides of second inner surface 205 in the longitudinal direction. Each protrusion 1413 includes a barb protruded feature, and two adjacent protrusions 1413 disposed side by side in the lateral direction of second inner surface 205 may have their pointing tip portions facing each other.

Protrusion 1412 may be provided at a center location along the longitudinal direction of first inner surface 204, although it may be provided at any other locations on first inner surface 204. When in the closed position, protrusion 1412 and protrusions 1413 create two cavities for trapping portions of the blood vessel or tissue structure that is being ligated. During operations, protrusion 1412 and first inner surface 204 push the blood vessel into the space between the two rows of protrusions 1413. The barb shaped protrusions 1413 may penetrate the blood vessel. This feature increases the force exerted to the blood vessel, and provides great grip of the blood vessel.

Although one protrusion 1412 is shown on first leg member 201, more than one protrusion 1412 may be longitudinally arranged on first inner surface 204. In addition, although two rows of protrusions 1413 are shown on second inner surface 205, more than two rows (e.g., three, four, five, etc.) of protrusions 1413 may be disposed on second inner surface 205.

FIG. 25C is a top view of second inner surface 205. The top view shows the arrangement and dimension of protrusions 1413. Protrusions 1413 are shown to be arranged in two rows, although they may be arranged in one or more than two rows. A length of each protrusion 1413 in the longitudinal direction of second inner surface 205 is designated as L8, and a width in the lateral direction is designated as b8. The ratio between L8 and b8 is greater than or equal to 1.0, such as 1.5, 2.0, 2.5, 3.0, 3.5, 4.0, or any other suitable number. Other features included in other embodiments shown in FIGS. 3A-24C discussed above may also be included in the embodiment shown in FIGS. 25A-25C. Detailed descriptions of such features are not repeated.

FIGS. 26A-26C show a perspective view, a cross sectional view, and a top view of an inner surface of another embodiment of surgical clip 200. FIG. 26A is a perspective view of surgical clip 200. Surgical clip 200 shown in FIG. 26A may include features similar to those shown in FIG. 3A and other figures, such as any of FIGS. 3B-25C, except that the protrusions provided on at least one of the inner surfaces of the two leg members have a different shape. FIG. 26A shows that first inner surface 204 is provided with two protrusions 1512, and second inner surface 205 is provided with a plurality of protrusions 1513. Each of protrusions 1512 may be a single piece extended in the longitudinal direction of first inner surface 204.

FIG. 26B is a cross sectional view of surgical clip 200 when first and second leg members 201 and 202 are brought closer to each other. FIGS. 256-26B show that protrusions 1513 have the barb protruded features and are disposed at two sides of second inner surface 205 in the longitudinal direction. Each protrusion 1513 includes a barb protruded feature, and two adjacent protrusions 1513 disposed side by side in the lateral direction of second inner surface 205 may have their pointing tip portions facing each other. Two protrusions 1512 may be provided at two sides of first inner surface 204 along the longitudinal direction. Each protrusion 1512 faces a row of protrusions 1513 on second inner surface 205 in a closed position, as shown in FIG. 26B.

When in the closed position, protrusions 1512 and protrusions 1513 create a cavity for trapping a portion of the blood vessel or tissue structure that is being ligated. During operations, protrusions 1512 and protrusions 1513 push the blood vessel into the cavity between the first and second inner surfaces 204 and 205. In addition, protrusion 1512 may push protrusion 1513 around the tissue causing deflection of the protruding feature 1513 which provides further resistance to the migration or sliding of the blood vessel relative to surgical clip 200 (or migration or sliding of surgical clip 200 relative to the blood vessel). The barb shaped protrusions 1513 may penetrate the blood vessel while the clip legs 201 and 202 are being closed. When the surgical clip 200 is opened, the barb shaped protrusions 1513 may release the blood vessel that is being ligated.

Although two protrusions 1512 are shown on first leg member 201, more than two (e.g., three, four, five, etc.) protrusions 1512 may be longitudinally arranged on first inner surface 204. In addition, although two rows of protrusions 1513 are shown on second inner surface 205, more than two rows (e.g., three, four, five, etc.) of protrusions 1513 may be disposed on second inner surface 205.

FIG. 26C is a top view of second inner surface 205. The top view shows the arrangement and dimension of protrusions 1513. Protrusions 1513 are shown to be arranged in two rows, although they may be arranged in one or more than two rows. A length of each protrusion 1513 in the longitudinal direction of second inner surface 205 is designated as L9, and a width in the lateral direction is designated as b9. The ratio between L9 and b9 is greater than or equal to 1.0, such as 1.5, 2.0, 2.5, 3.0, 3.5, 4.0, or any other suitable number. Other features included in other embodiments shown in FIGS. 3A-25C discussed above may also be included in the embodiment shown in FIGS. 26A-26C. Detailed descriptions of such features are not repeated.

Figure 27A:
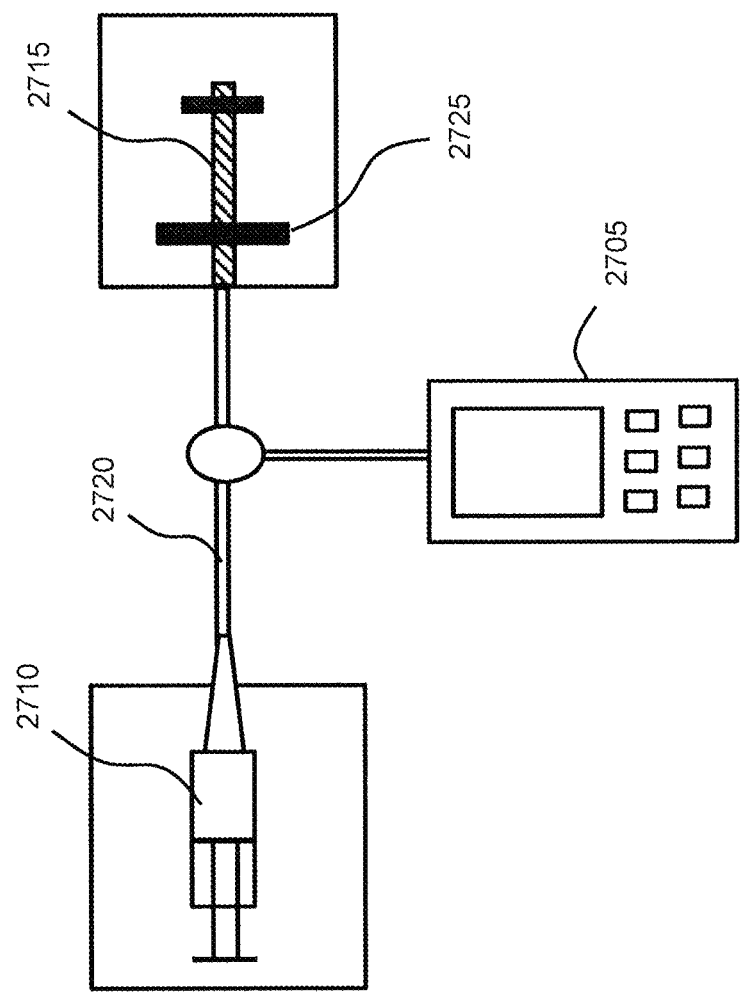
FIG. 27A shows testing set up for measuring the vessel occlusion.

The inventor has compared the prior art clips, such as the clips disclosed in the '846 patent and the '454 publication, and various embodiments of the disclosed surgical clips to evaluate the vessel occlusion (i.e., the pressure required to make the clip leak or break) and migration resistances (i.e., the force required to make the clip slip on the vessel or tissue). FIG. 27A shows the testing set up for measuring the vessel occlusion. As shown in FIG. 27A, vessel occlusion was measured by attaching a pressure sensor 2705 in-line with a pump 2710 and a ligated vessel 2715. In the test, a porcine vessel 2715 was obtained and sutured to a silastic tubing 2720, which was connected to a syringe pump 2710 that intermittently raised the pressure of the vessel much like physiological conditions. The vessel 2715 is fixed by a vessel testing fixture 2725.

Figure 27B:
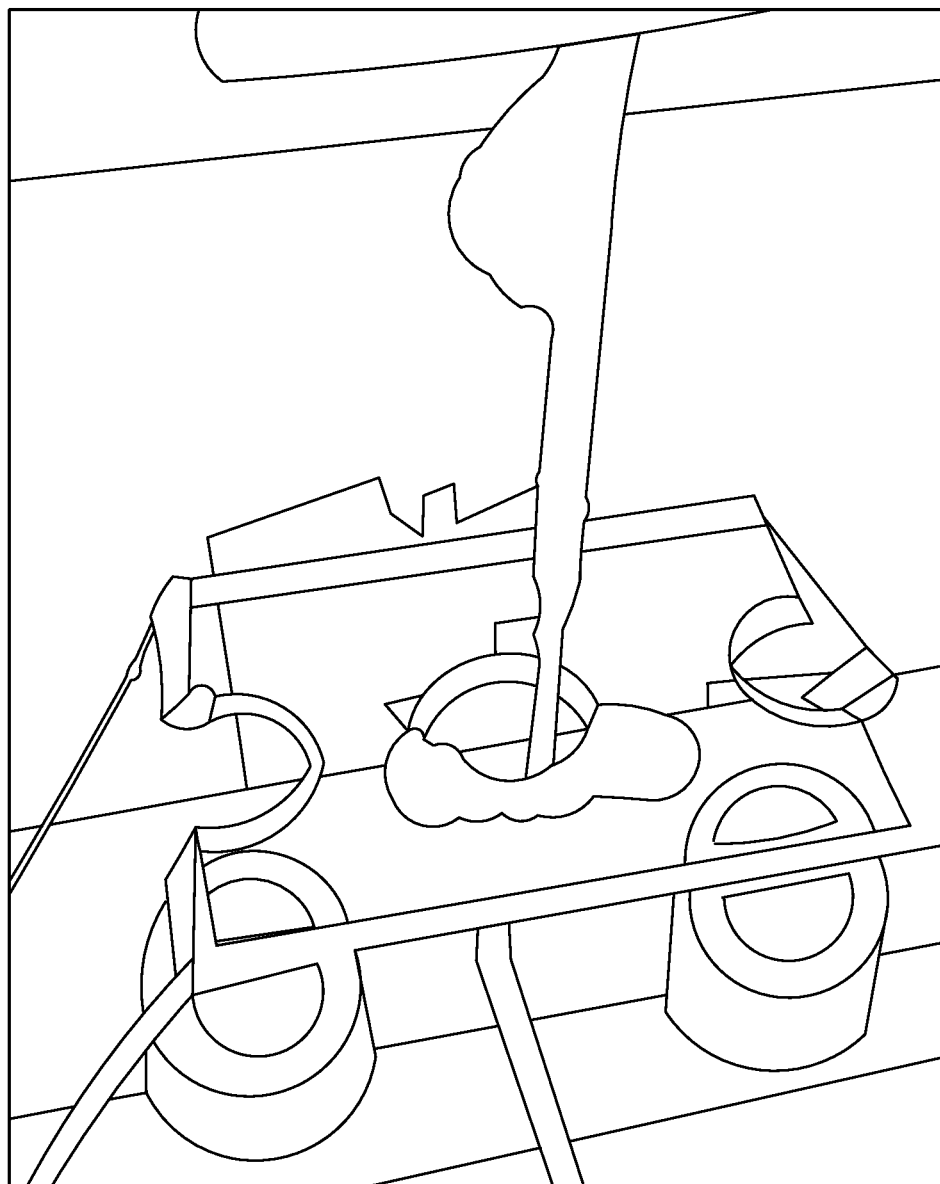
FIG. 27B shows a specially designed migration fixture for measuring migration resistance.

FIG. 27B shows a specially designed migration fixture for measuring migration resistance. Migration resistance was measure with universal testing equipment and the specially designed migration fixture. This fixture held the surgical clip in a stationary position as the vessel was pulled away from the surgical clip by a universal tester. The results are listed in Table 1. Table 1 shows the experimental test performed on a 3 mm vessel comparing the vessel occlusion and migration resistance of a prior art product (e.g., commercial product currently available) and a surgical clip made consistent with one embodiment of the present disclosure that includes a gable structure.

TABLE 1

|  | Vessel Occlusion (psi) | Migration Resistance (N) |
| --- | --- | --- |
| Commercial Product | 8.62 ± 1.52 | 0.49 ± 0.31 |
| Present Embodiment | 11.40 ± 2.78 | 2.17 ± 0.48 |

Figure 28:
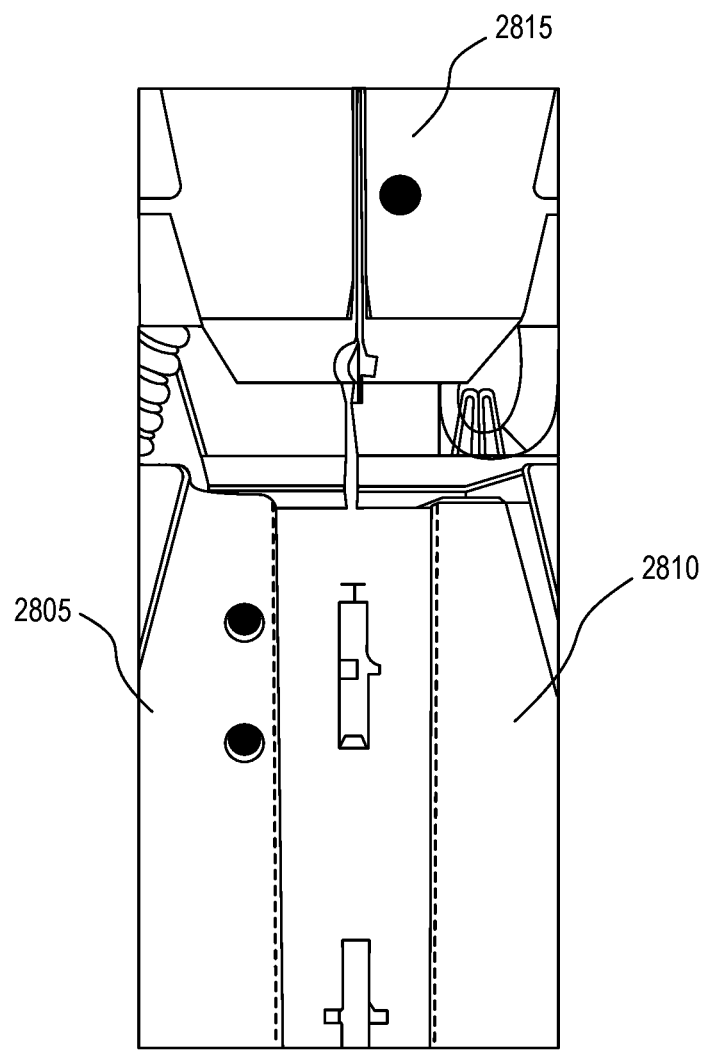
FIG. 28 shows a special fixture for testing the migration resistance of the disclosed protrusions and the prior art protrusions.

Furthermore, migration resistance testing was performed on prototype extruded surfaces using simulated vessels. This way a variety of configurations may be compared. In this test, two plates were manufactured with the migration resistant features to be tested on each side. FIG. 28 shows a special fixture for testing the migration resistance of the disclosed protrusions and the prior art protrusions. The special fixture held two plates 2805 and 2810 together, with the migration features on each plate facing each other at a fixed distance to more accurately compare the anti-migration effects of different designs of protrusions. Using this method, a variety of designs can be quickly evaluated by manufacturing different pairs of plates.

A simulated vessel is closed upon by the two plates that are separated at a fixed distance. Once the vessel is fixed (e.g., clamped) by the two plates 2805 and 2810, it is pulled by a device 2815 at a constant rate in a direction parallel to the plates and the force is measured. The maximum resistance force and failure modes are then recorded. The failure modes in this test include a mode in which the simulated vessel slipped from between the plates (i.e., the "sliding mode") and a mode in which the simulated vessel broke in an area not closed upon by the two plates (i.e., the "breaking mode"). High rates of vessel breaking modes (or low rate of vessel sliding modes) were observed with the protrusions made according to the present disclosure and the '846 patent, which means a high percentage of tested vessels broke rather than slid away from the plates having the protrusions made according to the present disclosure and the '846 patent. In addition, FIG. 29 shows a Table 2 which shows the migration resistance measured for prototyped protrusions using a simulated blood vessel.

As shown in Table 2, for the protrusions made according to the '846 patent, 67% of the tested vessels broke, and 33% of the tested vessels slid away from the plates 2805 and 2810. For the protrusions made according to the '454 publication, all of the tested vessels slid away from the plates 2805 and 2810. For the protrusions made according to the gable structure of the present disclosure, all of the tested vessels broke, and none of the tested vessels slid away from the plates 2805 and 2810. Also shown in Table 2 are the maximum resistance forces of various designs. The protrusions made according to the '454 publication has the lowest maximum resistance force of about 4 Newtons. The protrusions made according to the '846 patent has a much larger maximum resistance force of about 18 Newtons, which is more than 4 times of the force of the protrusions made according to the '454 publication. The protrusions having the gable structure according to the present disclosure has a largest maximum resistance force among the three designs, which is about 21 Newtons. As shown in Table 2, the disclosed protrusions having the gable structure provide increased migration resistance against sliding along the longitudinal direction of the vessels or tissue structures being ligated.

While illustrative embodiments have been described herein, the scope of the present disclosure covers any and all embodiments having equivalent elements, modifications, omissions, combinations (e.g., of aspects across various embodiments), adaptations and/or alterations as would be appreciated by those skilled in the art based on the present disclosure. For example, features included in different embodiments shown in different figures may be combined. The limitations in the claims are to be interpreted broadly based on the language employed in the claims and not limited to examples described in the present specification or during the prosecution of the application. The examples are to be construed as non-exclusive. It is intended, therefore, that the specification and examples be considered as illustrative only, with a true scope and spirit being indicated by the following claims and their full scope of equivalents.

What is claimed is:

1. A surgical clip for ligating a blood vessel or tissue structure, comprising:

a first leg member including a first inner surface and a first plurality of protrusions disposed on the first inner surfaces;

a second leg member including a second inner surface and a second plurality of protrusions disposed on the second inner surface; and a hinge member joining the first leg member and the second leg member, wherein at least one of the first and second plurality of protrusions includes a gable structure that extends along a longitudinal direction of the first or second inner surface, and when the first and second leg members are in a closed position, two protrusions on opposite leg members at corresponding lateral positions are disposed side by side with each other, with each protrusion facing a portion of the first or second inner surface on an opposite leg member.

2. The surgical clip of claim 1, wherein the gable structure includes a length in the longitudinal direction and a width in a lateral direction of the first or second inner surface, the length being greater than or equal to the width.

3. The surgical clip of claim 2, wherein the first or second inner surface includes a width, and the width of the gable structure is about 30%-70% of the width of the first or second inner surface.

4. The surgical clip of claim 1, wherein the gable structure has a triangular prism shape that includes a triangular cross section and an apex edge extending along the longitudinal direction, or wherein when the first and second leg members are in a closed position, the gable structure faces a portion of the first or second inner surface on an opposite leg member, and the apex edge corresponds to a longitudinal center line of the portion of the first or second inner surface.

5. The surgical clip of claim 4, wherein when the first and second leg members are in a closed position, the apex edge is in close proximity to the portion of the first or second inner surface, wherein the portion of the first or second inner surface is a planar surface, wherein when the first and second leg members are in a closed position, the gable structure faces a portion of the first or second inner surface on an opposite leg member, or wherein the portion of the first or second inner surface is a planar surface that includes a recess for receiving the apex edge.

6. The surgical clip of claim 1, wherein when the first and second leg members are in a closed position, the at least one of the first or second plurality of protrusions faces a portion of the first or second inner surface on an opposite leg member, or wherein when the first and second leg members are in a closed position, one or more of the first plurality of protrusions are disposed side by side with one or more of the second plurality of protrusions.

7. The surgical clip of claim 1, wherein the first plurality of protrusions is arranged in at least two rows on the first inner surface in the longitudinal direction of the first inner surface, each row including an alternating pattern that includes at least one of the first plurality of protrusions and at least one portion of the first inner surface, wherein the second plurality of protrusions is arranged in at least two rows on the second inner surface in the longitudinal direction of the second inner surface, each row including an alternating pattern that includes at least one of the second plurality of protrusions and at least one portion of the second inner surface, or wherein in the at least two rows on the first or second inner surface, each protrusion included in a first row is disposed side by side in a lateral direction with a portion of the first or second inner surface included in a second row.

8. The surgical clip of claim 1, wherein the two protrusions on opposite leg members disposed side by side and the portions of the first and second inner surfaces facing the two protrusions define a cavity between the two protrusions.

9. The surgical clip of claim 8, wherein the cavity has a cross sectional shape of a rhombus or parallelogram type, or wherein at least one group of the first plurality of protrusions or the second plurality of protrusions occupies 30% or more of a total area of the first or second inner surface.

10. The surgical clip of claim 1, wherein at least one group of the first plurality of protrusions or the second plurality of protrusions is arranged in at least two rows along the longitudinal direction of the first or second inner surface, and wherein a gap between two adjacent protrusions in the longitudinal direction in the at least two rows is about zero.

11. The surgical clip of claim 1, wherein the first plurality of protrusions and the second plurality of protrusions have substantially the same dimension.

12. A surgical clip for ligating a blood vessel or tissue structure, comprising:

a first leg member including a first inner surface and a first plurality of protrusions disposed on the first inner surfaces;

a second leg member including a second inner surface and a second plurality of protrusions disposed on the second inner surface; and a hinge member joining the first leg member and the second leg member, wherein at least one of the first and second plurality of protrusions includes a gable structure that extends along a longitudinal direction of the first or second inner surface, the gable structure has a prism shape that includes an apex edge extending along the longitudinal direction, and when the first and second leg members are in a closed position, two protrusions on opposite leg members at corresponding lateral positions are disposed side by side with each other, with each protrusion facing a portion of the first or second inner surface on an opposite leg member.

* * * * *

UNITED STATES PATENT AND TRADEMARK OFFICE
CERTIFICATE OF CORRECTION

| | | |
|---|---|---|
| PATENT NO. | : 10,881,414 B2 | Page 1 of 1 |
| APPLICATION NO. | : 15/736473 | |
| DATED | : January 5, 2021 | |
| INVENTOR(S) | : Richard Joseph Lebens, III | |

It is certified that error appears in the above-identified patent and that said Letters Patent is hereby corrected as shown below:

On the Title Page

Item (73), delete "Assignee: "NANOYA BIOMATERIALS, INC." and insert --Assignee: NANOVA BIOMATERIALS, INC.--.

Signed and Sealed this
Ninth Day of February, 2021

Drew Hirshfeld
*Performing the Functions and Duties of the
Under Secretary of Commerce for Intellectual Property and
Director of the United States Patent and Trademark Office*